United States Patent [19]

Cigan et al.

[11] Patent Number: 5,792,853

[45] Date of Patent: Aug. 11, 1998

[54] REVERSIBLE NUCLEAR GENETIC SYSTEM FOR MALE STERILITY IN TRANSGENIC PLANTS

[75] Inventors: Andrew M. Cigan; Marc C. Albertsen, both of Des Moines, Iowa

[73] Assignee: Pioneer Hi-Bred International, Inc., Des Moines, Iowa

[21] Appl. No.: 470,354

[22] Filed: Jun. 7, 1995

Related U.S. Application Data

[63] Continuation of Ser. No. 351,899, Dec. 8, 1994.

[51] Int. Cl.[6] .................... C07H 21/02; C07H 21/04; C12N 15/00; C12N 15/05

[52] U.S. Cl. .................... 536/24.1; 536/23.1; 536/23.6; 800/205; 800/DIG. 56; 47/58; 47/DIG. 1; 435/172.3; 935/10

[58] Field of Search .................... 800/200, 205; 47/58; 435/172.3, 172.1; 536/27.1, 24.1, 23.1, 23.6; 935/10

[56] References Cited

U.S. PATENT DOCUMENTS

| | | | |
|---|---|---|---|
| 4,407,956 | 10/1983 | Howell | 435/172 |
| 4,536,475 | 8/1985 | Anderson | 435/172.3 |
| 4,684,611 | 8/1987 | Schilperoort | 435/172.3 |
| 5,409,823 | 4/1995 | Crossland et al. | 435/172.3 |
| 5,510,474 | 4/1996 | Quail et al. | 536/24.1 |

FOREIGN PATENT DOCUMENTS

| | | | |
|---|---|---|---|
| 067 553 A2 | 12/1982 | European Pat. Off. | |
| 116 718 A1 | 8/1984 | European Pat. Off. | |
| 237 356 A2 | 9/1987 | European Pat. Off. | |
| 270 822 A1 | 6/1988 | European Pat. Off. | |
| 275 069 A2 | 7/1988 | European Pat. Off. | |
| WO 85/01856 | 5/1985 | WIPO | |
| 90/08830 | 8/1990 | WIPO | 435/172.3 |
| 92/04454 | 3/1992 | WIPO | 435/172.3 |

OTHER PUBLICATIONS

Kirnos et al. N6 methylation in mitochondrial DNA of higher plants. Biosis BA87:119396, 1988.

Vanyushin et al. ibid Biosis BR35:67871, 1988.

Armstrong et al. "Development and Availability of Germplasm with High Type II Culture Formulation Response," *Maize Genet Coop Newsletter* 65:92–93 (1991).

Bellomy et al. "A Method for Horizontal Polyacrylamide Slab Gel Electrophoresis," *Bio Techniques* 7(1):18–21 (1989).

Brooks et al. "The Isolation and Characterization of the Escherichia coli DNA Adenine Methylase (dam) Gene," *Nucl. Acids Res.* 11(3):837–51 (1983).

An et al. "Functional Analysis of the 3'Control Region of the Potato Wound–Inducible Proteinase Inhibitor II Gene," *Plant Cell* 1:115–122 (1989).

Bowen "Anthocyanin Genes as Visual Markers in Transformed Maize Tissues," in *GUS Protocols: Using the GUS Gene as a Reporter of Gene Expression* S.R. Gallagher ed., pp. 163–177 (Academic Press 1992).

Brent et al. "A Eukaryotic Transcriptional Activator Bearing the DNA Specificity of a Prokaryotic Repressor," *Cell* 43:729–736 (1985).

Chen et al. "Amino Acid Microsequencing of Internal Tryptic Peptides of Hemoregulated Eukaryotic Initiation Factor 2αSubunit Kinase; Homology to Protein Kinases," *P.N.A.S., USA* 88:315–319 (1991).

Colasanti et al. "Isolation and Characterization of cDNA Clones Encoding a Functional p34$^{cdc2}$Homologue from Zea Mays," *P.N.A.S., USA* 88:337–3381 (1991).

DeWet et al. "Firefly Luciferase Gene: Structure and Expression in Mammalian Cells," *Mol. Cell. Biol.* 7(2):725–737 (1987).

Farmer et al. "Extreme Evolutionary Consevation of QM, a Novel c–Jun Associated Transcription Factor," *Hum. Molec. Gen.* 3(5):723–728 (1994).

Fromm et L. "Inheritance and Expression of Chimeric Genes in the Progeny of Transgenic Maize Plants," *Bio/Technology* 8:833–839 (1990).

Dennis et al. "Molecular Analysis of the Alcohol Dehydrogenase (Adhl) Gene of Maize," *Nucl. Acids Res.* 12(9):3983–4000 (1984).

Gallie et al. "The 5'Leader Sequence of Tobacco Mosaic Virus RNA Enhances the Expression of Foreign Gene Transcripts in vitro and in vivo," *Nucl. Acids Res.* 15(8):3257–3273 (1987).

Gardner et al. "The Complete Nucleotide Sequence of an Infectious Clone of Cauliflower Nosaic Virus by M13mp7 Shotgun Sequencing," *Nucl. Acids Res.* 9(12):2871–2888 (1981).

Goff et al. "Identification of Functional Domains in the Maize Transcriptional Activator C1: Comparison of Wild–type and Dominant Inhibitor Proteins," *Genes & Development* 5:298–309 (1991).

Goldberg et al. "Anther Development: Basic Principles and Practical Applications," *Plant Cell* 5:1217–1219 (1993).

Golemis et al. "Fused Protein Domains Inhibit DNA Binding by LexA," *Mol. Cell. Biol.* 12(7):3006–3014 (1992).

Gordon–Kamm et al. "Transformation of Maize Cells and Regeneration of Fertile Transgenic Plants," *Plant Cell* 2:603–618 (1990).

Herskowitz et al. "Functional Inactivation of Genes by Dominant Negative Mutations," *Nature* 329:219–222 (1987).

(List continued on next page.)

*Primary Examiner*—Gary Benzion
*Attorney, Agent, or Firm*—Foley & Lardner

[57] ABSTRACT

Plant development can be altered by transforming a plant with a genetic construct that includes regulatory elements and DNA sequences capable of acting in a fashion to inhibit pollen formation or function, thus rendering the transformed plant reversibly male-sterile. In particular, the present invention relates to the use of dominant negative genes and an anther-specific promoter. Male sterility is reversed by incorporation into a plant of a second genetic construct which represses the dominant negative gene. The invention also relates to novel DNA sequences which exhibit the ability to serve as anther-specific promoters in plants.

32 Claims, 18 Drawing Sheets

OTHER PUBLICATIONS

Koltunow et al. "Different Temporal and Spatial Gene Expression Patterns Occur During Anther Development," *Plant Cell* 2:1201–1224 (1990).

Register et al. "Structure and Function of Selectable and Non–selectable Transgenes in Maize After Introduction by Particle Bombardment," *Plant Mol. Biol.* 25:951–961 (1994).

Shimamoto et al. "Fertile Transgenic Rice Plants Regenerated from Trnasformed Protoplasts," *Nature* 338:274–276 (1989).

Su et al. "A Multisite–directed Mutagenesis Using T7 DNA Polymerase: Application for Reconstructing a Mammalian Gene," *Gene* 69:81–89 (1988).

Czako et al. "Expression of DNA Coding for Diphtheria Toxin Chain A is Toxic to Plant Cells," *Plant Physiol* 95:687–692 (1991).

Thompson et al. "Characterization of the Herbicide–resistance Gene bar from Streptomyces Hygroscopicus," *EMBO Journal* 6(9):2519–2523 (1987).

Droge, et al. "Transgenic plants containing the phosphinothricin–N–acetyltransferase gene metabolize the herbicide L–phosphinothricin (glufosinate) differently form untransformed plants," *Plants* 187:142–151 (1992).

FIG. 1

```
   1 TTTTTATCTT TCTGATTTCA ACCATTACCG ATGAATTTCT ATTTGGATTA
  51 GTTCATTTTC GTCTTCCCTG TCTGATCCTG TTTTCGACAA TTCTGATCCC
 101 GAATCCGTTT TTGAATTAAA ATATAAAAAA TAAAAACAAG AAATGGTTTA
 151 TCTCGGTCAA TTTCGTTTTT CGCGAGGAAC ATATTCGGTG TACATGAGCC
 201 TTTGGTGCAC ATGAACTAAC AAAGTTCACA AAAAATTCTG AAAAAAAATC
 251 ATACATATTC TTTGCATCGC TACTCCTATT ATATATAAAA TTTCATGTTC
 301 AAATTTGTTA TATTTTAGCT GTAATAAAAA GAGTATTTTT AGCCGATTTT
 351 CTAATTTAAA CTTGTCAGAA GTTGTCTTTT TTTATTACAA CTAAGTTTAA
 401 TGAATTTGAA CTTGAAACAT GTATATAATT AGAGTAAGAT GAAAAGAATA
 451 TGTATGGATT TTTTCAAAAA AATTGTAAAC CTTTTTTAGT TCATGTGCAC
 501 CATATGTGAA TCAAAGGTTC ATATACACCG ATATGTTTC CTTTTTCACG
 551 AACCTAATCT GGCCTAGCCA GTATGTTGTG GACTTGGCTC CTAAGTGTGA
 601 ACCTGGCAGT GATGGGCAAC AAAGCAGGCA TGCCTTATGT GTGATGAATA
 651 ATTGACACAT GTACCGAGAG GTTTGGGGTT TTTTTGTATT GCATAGCAAA
 701 ACATGGTGAA ATTCTTAGGG TATTTTTGAG ATTACATTTA GGGCATGTTT
 751 GTTTCCCTTC ATTTTGAGGA ATTGGAATCT AACTAATAAA TTAGGCTATT
 801 TTTTTAGAAT GTGACATTCC CAACTTTCTA AAGTGTACAT ATAAGTCTAT
 851 CTTAAATAAT TTATAGGGTG GAAGATGTAA ATTGATTATA TAGATTTATA
 901 AGCTTCTTTT CTAATGTAAA ATTTAAAGCT CACTCTTCTA CTTGCTTCTC
 951 TATAACATAA TATAGTTTAT AACTACCTCT CTCATATGAT TTAGAATAAT
1001 ATACAAATAT ATTACATAAA AAATATATTA ATTGAATTAG TGTTGTCTAA
1051 TTTATAATTA TTAGAATGTA ATTCAATTCC AACGAAACAA CGGGGCCTTA
1101 GGTTTAATAT CTTCCTTACA CTGCGAAAAT GTTGTTACAC TTGCCAAAAA
1151 AAATCAATCG CATATTTACC TTACAAGGAC ATATTTTAGC AAAATGCTAT
1201 AGACATGAAT CCAACGTAAT CAATAGAGTG AGATTTACTG GTAAACTACC
1251 AATTGCTCAT CTGCTCGGTA CCAACCAGCC TTTCCTATTA CCATGCACAT
1301 GTTGCCTCTC AACTGCAGCA TCTTTCAAGC CGTGAGCAGA CATGTTGCAG
1351 ATCGAAGTAA GGTATATATG TGCATAGTCT CCTAATTCTT CATCTTCAAC
1401 CTCTAGCTGA TTGATCTCTG GTATTTACCA CTCTTTCCTT CCTTCCTTCC
1451 TTCAATTCTA AATACCACAA ATCAAAGTTG CTTTGCGATG
```

FIG. 18

```
   1 GGAATTCGGC ACGAGCTCGG TGCCGCCTTC CTTCCTTCAA TTCTAAATAC
  51 CACAAATCAA AGTTGCTTTG CGATGGTGAG CAGCAGCATG GACACGACGA
 101 GTGACAAGCG TGCGTCATCC ATGCTGGCCC CTAACCCTGG CAAGGCCACG
 151 ATCCTCGCCC TTGGCCACGC CTTCCGCAG CAGCTTGTCA TGCAGGACTA
 201 CGTCGTCGAC GGCTTCATGA AGAACACCAA CTGTGACGAC CCGGAGCTCA
 251 AGGAGAAGCT CACCAGACTC TGCAAGACGA CGACCGTGAG GACTCGGTAC
 301 GTGGTGATGT CGGATGAGAT CCTCAAGAAC TACCCGGAGC TGGCCCAGGA
 351 GGGGCTGCCG ACGATGAACC AGCGTCTGGA CATCTCGAAC GCGGCGGTGA
 401 CGCAGATGGC GACGGAGGCG TCCCTGTCGT GCGTCCGCTC GTGGGCGGC
 451 GCGCTCTCGT CCATTACCCA CCTGGTGTAC GTCTCGTCGA GCGAGGCGCG
 501 CTTCCCGGGC GGCGACCTGC ACCTGGCGCG CGCGCTGGGG CTGAGCCCGG
 551 ACGTCCGCCG CGTCATGCTG GCCTTCACCG GCTGCTCGGG CGGCGTGGCG
 601 GGGCTCCGCG TGGCCAAGGG CCTGGCCGAG AGCTGCCCGG GCGCGCGCGT
 651 GCTGCTGGCC ACCTCCGAGA CCACCATCGT GGGGTTCCGC CCGCCCAGCC
 701 CCGACCGCCC CTACGACCTC GTGGGCGTGG CGCTCTTCGG CGACGGCGCG
 751 GGCGCCGCCG TCATCGGCAC CGACCCCGCC CCGCCGAGC GCCCGCTCTT
 801 CGAGCTCCAC TCGGCGCTCC AGCGCTTCCT CCCGGACACG GAGAGGACCA
 851 TCGAGGGCCG GCTGACGGAG GAAGGCATCA AGTTCCAGCT GGGGCGGGAG
 901 CTGCCCCACA TCATCGAGGC GCACGTGGAG GACTTCTGCC AGAAGCTGAT
 951 GAAGGAGCGG CAGAGCGGCG AGGACGCCGA CGGTGGCGGC CCCGAGCCGA
1001 TGAGCTACGG GGACATGTTC TGGGCGGTCC ACCCCGGCGG GCCGGCCATC
1051 CTAACCAAGA TGGAGGGGCG CCTGGGCCTC GGCGCCGACA AGCTCCGCGC
1101 CAGCCGGTGC GCGCTCCGGG ACTTCGGCAA CGCCAGCAGC AACACCATCG
1151 TGTACGTGCT GGAGAACATG GTGGAGGACA CCCGGCGGAG GAGGCTGCTG
1201 GCTGCTGACG ACGGTGGAGA GGACTGCGAG TGGGGTCTCA TCCTCGCGTT
1251 CGGGCCGGGG ATCACGTTCG AGGGCATCCT AGCCAGGAAC TTGCAGGCAA
1301 CCGCGCGCGC CTCAGCCCAG CTCTGATCAC CTCTTGCTGT GTTGCTTTTC
1351 TGCTTGCTCT GCACCTCTGC TTCCGTGTGA TTGCTGCTTT GAGGGAGAAT
1401 GCTGAGCATC AACATTGCTC ATGAGCATCA ATGAAATAAG GGGCCCCGAA
1451 ATTCACTGCT CAAAAAAAAA AAAAAAAAAC TCGAG
```

REVERSIBLE NUCLEAR GENETIC SYSTEM FOR MALE STERILITY IN TRANSGENIC PLANTS

This is a continuing application based on Ser. No. 08/351,899, filed Dec. 8, 1994, from which priority under 35 USC § 120 is claimed.

BACKGROUND OF THE INVENTION

Plant development can be altered, according to the present invention, by transforming a plant with a genetic construct that includes regulatory elements and structural genes capable of acting in a cascading fashion to produce a reversible effect on a plant phenotype. A suitable construct includes a tissue specific promoter, a dominant negative gene, and a nucleotide sequence encoding a transcriptional activator linked to a DNA binding protein. In particular, the present invention relates to the use of a DAM-methylase gene as a dominant negative gene and an anther-specific promoter to produce transgenic plants that are reversibly male-sterile.

There is a need for a reversible genetic system for producing male sterile plants, in particular for autogamous plants. Production of hybrid seed for commercial sale is a large and important industry. Hybrid plants grown from hybrid seed benefit from the heterotic effects of crossing two genetically distinct breeding lines. The commercially desirable agronomic performance of hybrid offspring is superior to both parents, typically in vigor, yield and uniformity. The better performance of hybrid seed varieties compared to open-pollinated varieties makes the hybrid seed more attractive for farmers to plant and therefore commands a premium price in the market.

In order to produce hybrid seed uncontaminated with self-seed, pollination control methods must be implemented to ensure cross-pollination and to guard against self-pollination. Pollination control mechanisms include mechanical, chemical and genetic means.

A mechanical means for hybrid seed production can be used if the plant of interest has spatially separate male and female flowers or separate male and female plants. For example, a maize plant has pollen-producing male flowers in an inflorescence at the apex of the plant, and female flowers in the axiles of leaves along the stem. Outcrossing of maize is assured by mechanically detasseling the female parent to prevent selfing. Even though detasseling is currently used in hybrid seed production for plants such as maize, the process is labor-intensive and costly, both in terms of the actual detasseling cost and yield loss as a result of detasseling the female parent.

Most major crop plants of interest, however, have both functional male and female organs within the same flower, therefore, emasculation is not a simple procedure. While it is possible to remove by hand the pollen forming organs before pollen is shed, this form of hybrid production is extremely labor intensive and expensive. Seed is produced in this manner only if the value and amount of seed recovered warrants the effort.

A second general means of producing hybrid seed is to use chemicals that kill or block viable pollen formation. These chemicals, termed gametocides, are used to impart a transitory male-sterility. Commercial production of hybrid seed by use of gametocides is limited by the expense and availability of the chemicals and the reliability and length of action of the applications. A serious limitation of gametocides is that they have phytotoxic effects, the severity of which are dependent on genotype. Other limitations include that these chemicals may not be effective for crops with an extended flowering period because new flowers produced may not be affected. Consequently, repeated application of chemicals is required.

Many current commercial hybrid seed production systems for field crops rely on a genetic means of pollination control. Plants that are used as females either fail to make pollen, fail to shed pollen, or produce pollen that is biochemically unable to effect self-fertilization. Plants that are unable to self-fertilize are said to be "self-incompatible" (SI). Difficulties associated with the use of a self-incompatibility system include availability and propagation of the self-incompatible female line, and stability of the self-compatibility. In some instances, self-incompatibility can be overcome chemically, or immature buds can be pollinated by hand before the biochemical mechanism that blocks pollen is activated. Self-incompatible systems that can be deactivated are often very vulnerable to stressful climatic conditions that break or reduce the effectiveness of the biochemical block to self-pollination.

Of more widespread interest for commercial seed production are systems of pollen-control-based genetic mechanisms causing male sterility. These systems are of two general types: (a) genic male sterility, which is the failure of pollen formation because of one or more nuclear genes or (b) cytoplasmic-genetic male sterility, commonly referred to as "cytoplasmic male sterility" (CMS), in which pollen formation is blocked or aborted because of an alteration in a cytoplasmic organelle, which generally is a mitochondria.

Although there are hybridization schemes involving the use of CMS, there are limitations to its commercial value. An example of a CMS system, is a specific mutation in the cytoplasmically located mitochondria which can, when in the proper nuclear background, lead to the failure of mature pollen formation. In some instances, the nuclear background can compensate for the cytoplasmic mutation and normal pollen formation occurs. Specific nuclear "restorer genes" allow pollen formation in plants with CMS mitochondria. Generally, the use of CMS for commercial seed production involves the use of three breeding lines: a male-sterile line (female parent), a maintainer line which is isogeneic to the male-sterile line but contains fully functional mitochondria, and a male parent line. The male parent line may carry the specific restorer genes and, hence, is usually designated a "restorer line," which imparts fertility to the hybrid seed.

For crops such as vegetable crops for which seed recovery from the hybrid is unimportant, a CMS system can be used without restoration. For crops for which the fruit or seed of the hybrid is the commercial product, the fertility of the hybrid seed must be restored by specific restorer genes in the male parent or the male-sterile hybrid must be pollinated. Pollination of non-restored hybrids can be achieved by including with hybrids a small percentage of male fertile plants to effect pollination. In most species, the CMS trait is inherited maternally, since all cytoplasmic organelles are inherited from the egg cell only, and this restricts the use of the system.

CMS systems possess limitations that preclude them as a sole solution to production of male sterile plants. For example, one particular CMS type in maize (T-cytoplasm) confers sensitivity to the toxin produced by infection by a particular fungus. Although still used for a number of crops, CMS systems may break down under certain environmental conditions.

Nuclear (genic) sterility can be either dominant or recessive. Dominant sterility can only be used for hybrid seed formation if propagation of the female line is possible (for example, via in vitro clonal propagation). Recessive sterility can be used if sterile and fertile plants are easily discriminated. Commercial utility of genic sterility systems is limited however by the expense of clonal propagation and roguing the female rows of self-fertile plants.

Discovery of genes which would alter plant development would be particularly useful in developing genetic methods to induce male sterility because other currently available methods, including detasseling, CMS and SI, have shortcomings.

A search for methods of altering development in plants by use of genetic methods led to methylase genes of the present invention. Changes in the DNA methylation pattern of specific genes or promoters have accounted for changes in gene expression. Methylation of DNA is a factor in regulation of genes during development of both plants and animals.

Methylation patterns are established by methods such as the use of methyl-sensitive CpG-containing promoters (genes). In general, actively transcribed sequences are under methylated. In animals, sites of methylation are modified at CpG sites (residues). Genetic control of methylation of adenine (A) and cytosine (C) (nucleotides present in DNA) is affected by genes in bacterial and mammalian species. In plants, however, methyl moieties exist in the sequence CXG, where X can be A, C or T, where C is the methylated residue. Inactivation due to methylation of A is not known in plants, particularly within GATC sites known to be methylated in other systems.

Although there is no suggestion in the art that methylation might be induced in tissues specifically or otherwise, to achieve a desired end in a transgenic plant, it was known in the art that promoter methylation can cause gene inactivation, and alter the phenotype in transgenic organisms.

Envisioning directed methylation as a means for control of plant development, for example, to effect male sterility, would be discouraged by difficulties anticipated in using expression of a gene that has a generalized inactivating effect in a ubiquitous target, e.g., a methylase gene such as the E. coli DNA adenine methylase (DAM) for which GATC is a target, as a means to control a specific developmental step without otherwise deleteriously affecting the plant. The DAM target exists in many promoters, therefore, a problem of maintaining plant viability would be expected from inactivating promoters and/or genes that are crucial for cell viability. Unless there was a way to "compartmentalize" methylation introduced into a host system by an exogenous vector, methylation as an approach to producing male sterility by genetic means would not be expected to succeed. The present invention provides methods and compositions to compartmentalize and to manipulate genes such as DAM to effect changes in plant development.

SUMMARY OF THE INVENTION

The invention relates to an isolated DNA molecule comprising a nucleotide sequence of capable of regulating the expression of a DNA sequence in anther tissue when the DNA molecule is part of a recombinant DNA construct.

The isolated molecule may comprise the nucleotide sequence of the Sca-NcoI fragment of DP5055, a nucleotide sequence extending at least 503 base pairs upstream relative to the start codon at nucleotide position 1488 of FIG. 1, a nucleotide sequence extending from position–503 to position–1 upstream relative to the start codon at nucleotide position 1488 of FIG. 1, a nucleotide sequence extending from position–587 to position–1 upstream relative to the start codon at nucleotide position 1488 of FIG. 1, a nucleotide sequence extending from position–890 to position–1 upstream relative to the start codon at nucleotide position 1488 of FIG. 1, or a nucleotide sequence extending from position–503 to position–134 upstream relative to the start codon at nucleotide position 1488 of FIG. 1.

The invention further relates to a recombinant DNA construct comprising: a DNA sequence that encodes a gene product which, when expressed, inhibits pollen formation or function; an operator capable of controlling the expression of the DNA sequence; a gene encoding a DNA binding protein capable of binding to the operator and activating transcription of said dominant negative gene; and a tissue specific promoter operably linked to DNA sequence.

The recombinant DNA construct of the invention may also comprise: a DNA sequence encoding a gene product which when expressed in a plant inhibits pollen formation or function; an operator which controls the expression of said DNA sequence; and a promoter specific to cells critical to pollen formation or function operatively linked to said DNA sequence encoding a gene product. In further embodiments, the recombinant DNA construct may further comprise a selectable marker gene, a DNA sequence encoding a DNA binding region, or a DNA sequence encoding an activating domain.

In one embodiment, the gene product encoded by the DNA sequence of the recombinant DNA construct of the invention may be a cytotoxin. In another embodiment, the promoter may be an anther-specific promoter, and construct may comprise the constructs DP5814, DP6509, PHP8036, PHP8037, or PHP6520. In still another embodiment, the operator may be lexA operator. And, in yet another embodiment, the recombinant DNA construct may further comprise a selectable marker gene.

In another embodiment of the invention, the recombinant DNA construct comprises a DNA sequence encoding a DNA-binding protein, capable of binding to the operator of the recombinant DNA construct as defined above, and a promoter which controls expression of said DNA sequence. This recombinant DNA construct may further comprise a selectable marker gene. In one embodiment, the DNA binding protein of the recombinant DNA construct may be lexA protein. In another embodiment, the promoter may be specific to cells critical to pollen formation or function. In still another embodiment, the promoter may be an anther specific promoter, which may comprise the isolated DNA molecule as defined above. Still further, the promoter of this construct may be an inducible promoter or a constitutive promoters which may be maize ubiquitin promoter as the constitutive promoter. The recombinant DNA construct may be PHP6522 or PHP6555.

An additional aspect of the invention relates to is an expression vector comprising the isolated DNA molecule as defined above. The expression vector may further comprise a DNA sequence encoding a gene product, in which the DNA sequence is operably linked to the promoter. In one embodiment, the gene product of the expression vector disrupts the function or formation of pollen. In still another embodiment, the DNA sequence of the expression vector is heterologous with respect to the promoter. The invention also relates to a transgenic plant comprising the expression vector.

A further embodiment of the invention includes an anther specific promoter comprising a nucleotide sequence of promoter 5126f which exhibits the ability to control expression of a DNA sequence encoding a gene product. In one embodiment of the invention the gene product inhabits the function or formation of pollen. In another embodiment, the gene product comprises a cytoxin.

Yet another aspect of the invention relates to a method for producing reversible male sterility in plants. The method comprises the steps (a) transforming a first plant with an recombinant DNA construct such that the plant exhibits male sterility, the construct comprising (i) a lexA operator controlling the expression of a DNA sequence that encodes a gene product which inhibits the function or formation of pollen, the operator embedded in a tissue specific promoter which is operatively linked to the DNA sequence, and (ii) a DNA sequence encoding a lexA repressor, the DNA sequence operatively linked to an inducible promoter; and (b) exposing the plant to an inducer to reverse the male sterile effect of the construct. In further embodiments, the tissue specific promoter may be an anther-specific promoter. In another embodiment of the invention, the anther-specific promoter may comprise a nucleotide sequence of promoter 5126 which exhibits the ability to control expression of a DNA sequence encoding a gene product. In yet another embodiment the gene product may be a dominant negative gene, which may be DAM-methylase.

Also, the present invention relates to a male sterile plant and a method of producing a male sterile plant which comprises: (a) introducing into the genome of a pollen producing plant capable of being genetically transformed a recombinant DNA molecule comprising (i) a DNA sequence encoding a gene product which when expressed in a plant inhibits pollen formation or function, (ii) an operator which controls the expression of the DNA sequence, and (iii) a promoter specific to cells critical to pollen formation or function operatively linked to the DNA sequence encoding a gene product; and (b) growing said pollen-producing plant under conditions such that male sterility is achieved as a result of the expression of the DNA sequence. In further embodiments of this aspect of the invention the gene product may be a cytotoxin. In still another embodiment, the promoter of the invention may be an anther-specific promoter. In yet another embodiment, the anther-specific promoter may comprise a nucleotide sequence of promoter 5126 which exhibits the ability to control expression of a DNA sequence encoding a gene product. In yet another embodiment, the operator may be lexA operator. The method of producing a male sterile plant may further comprise a selectable marker gene.

The invention further relates to hybrid seed and a method of producing hybrid seed from a male sterile plant which comprises (a) introducing into the genome of a pollen producing plant capable of being genetically transformed a recombinant DNA molecule comprising (i) a DNA sequence encoding a gene product which when expressed in a plant inhibits pollen formation or function, (ii) an operator which controls the expression of the DNA sequence, and (iii) a promoter specific to cells critical to pollen formation or function operatively linked to the DNA sequence encoding a gene product; (b) growing the pollen-producing plant under conditions such that male sterility is achieved as a result of the expression of the DNA sequences; (c) crossing the male sterile plant with pollen derived from a male fertile line, the pollen having integrated into its genome a recombinant DNA molecule comprising a DNA sequence encoding a DNA-binding protein and a promoter which controls expression of the DNA sequence, the protein capable of binding to the operator of the recombinant DNA of the male-sterile plant; and (d) harvesting the hybrid seed with restored fertility. In a further embodiment of this aspects of the invention, the gene product may be cytotoxin. In still another embodiment, the promoter may be an anther-specific promoter. In still another embodiment of the invention, the anther-specific promoter may comprise a nucleotide sequence of promoter 5126 which exhibits the ability to control expression of a DNA sequence encoding a gene product. In yet another embodiment, the operator may be lexA operator. The method of producing a male sterile plant may further comprise a selectable marker gene.

Also an aspect of the invention is a method of producing reversible male sterility in a plant which comprises: (a) introducing into the genome of a pollen producing plant capable of being genetically transformed a first recombinant DNA molecule comprising (i) a DNA sequence encoding a gene product which when expressed in a plant inhibits pollen formation or function, (ii) an operator which controls the expression of the DNA sequence, and (iii) a promoter specific to cells critical to pollen formation or function operatively linked to the DNA sequence encoding a gene product; (b) growing the pollen-producing plant under conditions such that male sterility is achieved as a result of the expression of the DNA sequences; and (c) crossing the male sterile plant with pollen derived from a male fertile line to form a hybrid plant which is male fertile, the pollen having integrated into its genome a second recombinant DNA molecule comprising a DNA sequence encoding a DNA-binding protein and a promoter which controls expression of the DNA sequence, the protein capable of binding to the operator of the recombinant DNA of the male-sterile plant. In further embodiments of this aspect of the invention the gene product may be cytotoxin. In still another embodiment, the promoter may be an anther-specific promoter. In yet another embodiment of the invention, the anther-specific promoter may comprise a nucleotide sequence of promoter 5126 which exhibits the ability to control expression of a DNA sequence encoding a gene product. In yet another embodiment, the operator may be lexA operator. In one embodiment, the first recombinant molecule or second recombinant DNA molecule may further comprises a selectable marker gene. In another embodiment of the invention, the DNA-binding protein may be lexA protein. In yet another embodiment, the promoter of the second recombinant DNA molecule is a promoter specific to cells critical to pollen formation or function, and may be an anther-specific promoter. The anther-specific promoter may comprise an isolated DNA molecule comprising a nucleotide sequence of capable of regulating the expression of a DNA sequence in anther tissue when the DNA molecule is part of an operable recombinant DNA construct. The promoter of the second recombinant DNA molecule may be an inducible promoter or a constitutive promoter, which may be maize ubiquitin promoter.

Another aspect of the present invention is a transformed plant cell, and a plant regenerated from such plant cell, containing an expression vector comprising an isolated DNA molecule comprising a nucleotide sequence of capable of regulating the expression of a DNA sequence in anther tissue when the DNA molecule is part of an operable recombinant DNA construct. The expression vector may further comprise a DNA sequence encoding a gene product, the sequence being operable linked to the promoter. The invention also relates to hybrid seed and make sterile plants produced by the methods of the invention.

In accordance with the present invention, two types of genetic systems have been combined in a transforming genetic construct to create a cascading mechanism to affect plant development. One system highlights a tissue-specific promoter which controls gene expression, e.g., expression of a transcriptional activator. The second system includes a DNA sequence that encodes a gene product which inhibits pollen formation or function, e.g., a dominant negative gene such as a methylase gene, the expression product of which disrupts pollen formation and function.

A specific component of the invention is a transforming genetic construct, incorporating elements of both of these systems, that includes regulatory elements and structural genes capable of interacting to cause a particular phenotype, depending on the specific regulators and genes present. By virtue of the presence of this construct in one parent plant, certain advantages of the present invention arise. For example, a one-step approach to achieving male sterility is implemented. For example, the present invention contemplates the use, in producing reversible male sterility in plants, of a genetic construct that contains a tissue-specific promoter, a dominant negative gene, and a specific stretch of DNA that encloses a transcriptional activator which is capable of activating the dominant negative gene. The present invention in one aspect thus provides a new, nuclear basis for manipulating male fertility.

More specifically, a genetic construct suitable for the present invention comprises a dominant negative gene and a specific stretch of DNA that, when positioned upstream of the dominant negative gene, controls expression of the dominant negative gene in association with a DNA binding gene and a promoter that controls expression at a specific time or times in development.

A dominant negative gene is one that, when expressed, effects a dominant phenotype in the plant. Herskowitz (1987), used the term "dominant negative" to denote a gene that encodes a mutant polypeptide which, when overexpressed, disrupts the activity of the wild-type gene. A wild type gene is one from which the mutant derived. In the present description the phrase "dominant negative gene" is applied to a gene coding for a product that disrupts an endogenous genetic process of a host cell which receives the gene, and that is effective in a single copy or may produce an effect due to overexpression of the gene either by increased production of the gene product, or by coexpression of multiple copies of the gene. Exemplary of the class of dominant negative genes are cytotoxic genes, methylase genes, and growth-inhibiting genes. Dominant negative genes include diphtheria toxin A-chain gene (Czako and An, 1991), cell cycle division mutants such as CDC in maize (Colasanti, et al., 1991) the WT gene (Farmer, et al., 1994) and P68 (Chen, et al., 1991). Candidate genes for a dominant negative gene in the genetic constructs of the present invention are also exemplified by a DAM-methylase gene, such as the gene isolated from *E. coli*. A candidate gene may or may not be deleterious to the source from which it was derived. Indeed, a candidate gene may serve an essential function in its source.

In an illustrative embodiment, a candidate dominant negative gene which exploits genetic methylation to alter development of specific plant tissues is a DAM-methylase gene. This gene is used to inactivate a genetic region critical for pollen formation or function thereby causing a male sterile plant to form.

In particular, the components of a first genetic construct of the present invention are as follows:

A transcriptional activator, such as the maize C1 gene, is fused to a bacterial DNA binding protein such as lexA.

(Brent and Ptashne, 1985). This gene fusion, designated "lexA-C1," is placed under the control of an anther-specific promoter, such as the 5126 promoter. The genetic construct is designated as:

5126::lexA-C1 The DAM-methylase gene is placed behind a minimal 35S promoter containing the lexA binding site (Lex), as symbolized below:

35S-lexAop::DAM 35S-lexAop::DAM and 5126::lexA-C1 are two separate transcription units on the same plasmid, the plasmid preferably including a selectable marker gene.

A transgenic plant containing a construct of the present invention can be regenerated from a culture transformed with that same construct, so long as plant species involved is susceptible to regeneration.

A plant is regenerated from a transformed cell or culture, or from an explant, by methods disclosed herein and known to those of skill in the art. "Culture" in this context comprehends an aggregate of cells, a callus, or derivatives thereof that are suitable for culture. Methods vary according to the plant species. Seed is obtained from the regenerated plant or from a cross between the regenerated plant and a suitable plant of the same species using breeding methods known to those of skill in the art.

When a first construct, as that described above, is transformed into plants, the result is increased expression compared to the situation where transcription is controlled only by the anther-specific promoter of the DAM-methylase gene. The enhanced expression is due to production of the transcriptional activator lexA-C1, which specifically binds to the Lex operator and controls the expression of the DAM-methylase gene, effecting male sterility. The methods of the present invention are particularly attractive for expression of genes, such as those in maize, that when mutated confer a dominant negative phenotype. Gene products encoded by such genes generally require high expression in order to interfere with the function of the wild-type protein, e.g., the maize CDC21 gene.

To reverse this effect, a first plant having the first construct is mated with a second plant that contains a second construct including the 5126 or other suitable promoter, including other anther-specific promoters such as the 5126 deletion mutation promoters or constitutive promoters, fused to the lexA gene which expresses only the DNA binding protein lexA. This protein binds specifically to the LexA operator but does not activate gene expression. Rather, it represses expression, thus shutting off DAM-methylase gene expression and rendering a plant having both a first and a second genetic construct, male-fertile.

Pursuant to the present invention, another way to utilize the components of this system is to embed a lexA DNA binding site (i.e., lexA operator) in the tissue specific promoter 5126 and couple the expression of the lexA repressor to an inducible promoter. Any gene that is expressed due to transcription of the 5126 promoter is turned off (repressed) by applying a chemical which induces the expression of lexA. LexA repressor protein binds to the lexAop located in the 5126 promoter and, as a consequence of binding to this region of DNA, shuts off expression of the reporter gene. If, for example, this system is used with the DAM methylase gene, application of a chemical inducer reverses the sterile phenotype and renders the plant male-fertile.

By way of example, a suitable genetic construct contains the following components:

1. 5126::lexAop::DAM methylase;
2. [a promoter that is inducible by a hormone (auxin, salicylic acid), chemical safener and the like] ::lexA; and 3. a selectable marker, for instance which imparts herbicide or antibiotic resistance, or which effects complementation of amino acid or nucleic acid auxotrophs. When this construct is transformed into plants, the resulting phenotype is male-sterile in the absence of a chemical inducer. But application of inducing agent at the appropriate time results in male-fertile plants, eliminating the need for genetically crossing plants that contain the sterility constructs with plants that contain repressor constructs in order to restore fertility. (See U.S. Ser. No. 07/848,465.) Examples of herbicide resistance genes include BAR and PAT for glufosinate (bialophos) resistance.

When a construct of the present invention is linked with a selectable marker such as a herbicide resistance gene, the resulting construct enables a method to destroy segregating male fertile plants by applying a herbicide to the plants generated from crossing male-sterile plants with pollen from male fertile plants. Only the male sterile plants will survive.

Another way to utilize the components of this system in a recombinant DNA construct used to transform a plant is to embed an operator capable of controlling expression of a DNA sequence (e.g., a lexA operator), in a tissue specific promoter (e.g., the anther-specific promoter 5126); the tissue-specific promoter operatively linked to a DNA sequence that produces a gene product which inhibits pollen formation or function, e.g., a dominant negative gene such as DAM-methylase. To embed such an operator includes placing it (according to methods known to one skilled in the art) within, upstream or downstream of the nucleotide sequence of the promoters of the invention.

To reverse this effect, a plant transformed with such a construct is mated with a second plant that contains a second construct comprising the 5126 or other suitable promoter, including other anther-specific promoters such as the 5126 deletion mutation promoters or constitutive promoters, controlling the expression of a gene encoding a DNA-binding protein, e.g., the lexA gene which expresses the DNA binding protein lexA, which is capable of binding to the operator of the first construct. Specifically, the DNA-binding protein binds to the operator of the first construct and represses expression, thus shutting off expression of the DNA encoding a gene product which inhibits the function or formation of pollen and rendering a plant having both a first and a second genetic construct, male-fertile.

In a specific embodiment, LexA repressor protein produced by the second construct binds to the lexA operator embedded in the 5126 promoter in the first construct and, as a consequence of binding to this region of DNA, shuts off expression of the gene which inhibits pollen formation or function, e.g., a dominant negative gene such as DAM-methylase, and renders the transformed plant male-fertile.

When a construct of the present invention is linked with a selectable marker gene such as a herbicide resistance gene, the resulting construct enables a method to destroy segregating male fertile plants by applying a herbicide to the plants generated from crossing male-sterile plants with pollen from male fertile plants. Only the male sterile plants will survive.

According to another embodiment of the present invention, a genetic construct that has a methylase gene as the dominant negative gene operably linked to a tissue-specific promoter, such as the anther-specific 5126 promoter, is suitable for the practice of the present invention. A method for altering the development of a plant represents an aspect of the present invention. Such a method preferably comprises the steps of:

(a) transforming a plant with a genetic construct comprising a methylase gene and a suitable promoter; and
(b) growing the plant in an environment in which the methylase gene is expressed, thereby altering expression of a gene, or genes, essential for a developmental process by methylating its promoter.

To produce a male-sterile plant, the promoter allows gene expression only in a specific tissue, preferably a tissue critical for pollen formation or function, such as in the tapetum, in the anther or in early microspores. The construct may also include a methylase gene as the DNA sequence encoding a gene product capable of inhibiting pollen formation or function. A suitable methylase gene is a bacterial DAM (DNA adenine methylating) gene. Bacterial sources include *E. coli*. The DAM class of genes methylates a N6 position of adenine in the nucleotide sequence GATC. The construct includes a target DNA and is dominant negative because it represses the synthesis of mRNA by the target DNA.

A tissue-specific promoter is a promoter capable of controlling expression of a DNA sequence, for example a gene, in a specific tissue. For causing reversible male sterility in plants, promoters that are active in tissues directly or indirectly affecting pollen structure and/or function, are particularly suitable.

The search for tissue-specific promoters benefitted from the novel concept in plant genetics, of subtracting mutant from normal plant mRNA to result in mRNA differing from the normal in areas of the genome specifically related to the functions of interest in the present invention, anther development. An embodiment suitable for the present invention is an anther specific promoter, for example, the active DNA sequences of the novel plant promoter designated 5126.

Methods and compositions are described below for the production of male-sterile lines by the use of genetic constructs that include a methylase gene and a suitable promoter.

To correlate the insertion of a genetic construct of the present invention into a plant nuclear genome, with the male sterile phenotype of the plant, Southern blots of DNA of plants were analyzed. By this analysis, male sterility was found to be correlated with the presence of a genetic construct of the present invention.

In an embodiment of the invention, in order to destroy segregating male fertile plants so they do not grow in a field, a constitutive promoter is linked to a selectable marker and introduced into a plant with a genetic construct comprising a methylation gene regulated by a promoter. This system is useful when maintaining a sterile inbred line wherein a male fertile inbred plant is bred to a male-sterile plant of the same type. Seed harvested from the female male-sterile plant will segregate 1:1 for resistance to a selective agent. The plants may be sprayed with the selective agent; consequently, only the plants that have maintained the selectable marker gene survive. These plants are those that were transformed with the methylating construct.

The present invention also relates a male-sterile plant produced by methods of the present invention, and to the seed of such plants.

In accordance with the present invention, two types of genetic systems have been combined in a transforming genetic construct to create a cascading mechanism to affect plant development. One system highlights a tissue-specific promoter which controls gene expression, e.g., expression of a transcriptional activator. The second system includes a DNA sequence that encodes a gene product which inhibits pollen formation or function, e.g., a dominant negative gene such as a methylase gene, the expression product of which disrupts pollen formation and function.

A specific component of the invention is a transforming genetic construct, incorporating elements of both of these systems, that includes regulatory elements and structural genes capable of interacting to cause a particular phenotype, depending on the specific regulators and genes present. By virtue of the presence of this construct in one parent plant, certain advantages of the present invention arise. For example, a one-step approach to achieving male sterility is implemented. For example, the present invention contemplates the use, in producing reversible male sterility in plants, of a genetic construct that contains a tissue-specific promoter, a dominant negative gene, and a specific stretch of DNA that encloses a transcriptional activator which is capable of activating the dominant negative gene. The present invention in one aspect thus provides a new, nuclear basis for manipulating male fertility.

More specifically, a genetic construct suitable for the present invention comprises a dominant negative gene and a specific stretch of DNA that, when positioned upstream of the dominant negative gene, controls expression of the dominant negative gene in association with a DNA binding gene and a promoter that controls expression at a specific time or times in development.

A dominant negative gene is one that, when expressed, effects a dominant phenotype in the plant. Herskowitz (1987), used the term "dominant negative" to denote a gene that encodes a mutant polypeptide which, when over expressed, disrupts the activity of the wild-type gene. A wild type gene is one from which the mutant derived. In the present description the phrase "dominant negative gene" is applied to a gene coding for a product that disrupts an endogenous genetic process of a host cell which receives the gene, and that is effective in a single copy or may produce an effect due to overexpression of the gene either by increased production of the gene product, or by coexpression of multiple copies of the gene. Exemplary of the class of dominant negative genes are cytotoxic genes, methylase genes, and growth-inhibiting genes. Dominant negative genes include diphtheria toxin A-chain gene (Czako and An, 1991), cell cycle division mutants such as CDC in maize (Colasanti, et al., 1991) the WT gene (Farmer, et al., 1994) and P68 (Chen, et al., 1991). Candidate genes for a dominant negative gene in the genetic constructs of the present invention are also exemplified by a DAM-methylase gene, such as the gene isolated from *E. coli*. A candidate gene may or may not be deleterious to the source from which it was derived. Indeed, a candidate gene may serve an essential function in its source.

In an illustrative embodiment, a candidate dominant negative gene which exploits genetic methylation to alter development of specific plant tissues is a DAM-methylase gene. This gene is used to inactivate a genetic region critical for pollen formation or function thereby causing a male sterile plant to form.

In particular, the components of a first genetic construct of the present invention are as follows:

A transcriptional activator, such as the maize C1 gene, is fused to a bacterial DNA binding protein such as lexA. (Brent and Ptashne, 1985). This gene fusion, designated "lexA-C1," is placed under the control of an anther-specific promoter, such as the 5126 promoter. The genetic construct is designated as:

5126::lexA-C1 The DAM-methylase gene is placed behind a minimal 35S promoter containing the lexA binding site (Lex), as symbolized below:

35S-lexAop::DAM 35S-lexAop::DAM and 5126::lexA-C1 are two separate transcription units on the same plasmid, the plasmid preferably including a selectable marker gene.

A transgenic plant containing a construct of the present invention can be regenerated from a culture transformed with that same construct, so long as plant species involved is susceptible to regeneration.

A plant is regenerated from a transformed cell or culture, or from an explant, by methods disclosed herein and known to those of skill in the art. "Culture" in this context comprehends an aggregate of cells, a callus, or derivatives thereof that are suitable for culture. Methods vary according to the plant species. Seed is obtained from the regenerated plant or from a cross between the regenerated plant and a suitable plant of the same species using breeding methods known to those of skill in the art.

When a first construct, as that described above, is transformed into plants, the result is increased expression compared to the situation where transcription is controlled only by the anther-specific promoter of the DAM-methylase gene. The enhanced expression is due to production of the transcriptional activator lexA-C1, which specifically binds to the Lex operator and controls the expression of the DAM-methylase gene, effecting male sterility. The methods of the present invention are particularly attractive for expression of genes, such as those in maize, that when mutated confer a dominant negative phenotype. Gene products encoded by such genes generally require high expression in order to interfere with the function of the wild-type protein, e.g., the maize CDC21 gene.

To reverse this effect, a first plant having the first construct is mated with a second plant that contains a second construct including the 5126 or other suitable promoter, including other anther-specific promoters such as the 5126 deletion mutation promoters or constitutive promoters, fused to the lexA gene which expresses only the DNA binding protein lexA. This protein binds specifically to the LexA operator but does not activate gene expression. Rather, it represses expression, thus shutting off DAM-methylase gene expression and rendering a plant having both a first and a second genetic construct, male-fertile.

Pursuant to the present invention, another way to utilize the components of this system is to embed a lexA DNA binding site (i.e., lexA operator) in the tissue specific promoter 5126 and couple the expression of the lexA repressor to an inducible promoter. Any gene that is expressed due to transcription of the 5126 promoter is turned off (repressed) by applying a chemical which induces the expression of lexA. LexA repressor protein binds to the lexAop located in the 5126 promoter and, as a consequence of binding to this region of DNA, shuts off expression of the reporter gene. If, for example, this system is used with the DAM methylase gene, application of a chemical inducer reverses the sterile phenotype and renders the plant male-fertile.

By way of example, a suitable genetic construct contains the following components:

1. 5126::lexAop::DAM methylase;
2. [a promoter that is inducible by a hormone (auxin, salicylic acid), chemical safener and the like] ::lexA; and
3. a selectable marker, for instance which imparts herbicide or antibiotic resistance, or which effects complementation of amino acid or nucleic acid auxotrophs. When this construct is transformed into plants, the resulting phenotype is male-sterile in the absence of a chemical inducer. But application of inducing agent at the appropriate time results in male-fertile plants, eliminating the need for genetically crossing plants that contain the sterility constructs with plants that contain repressor constructs in order to restore fertility. (See U.S. Ser. No. 07/848,465.) Examples of herbicide resistance genes include BAR and PAT for glufosinate (bialophos) resistance.

When a construct of the present invention is linked with a selectable marker such as a herbicide resistance gene, the resulting construct enables a method to destroy segregating male fertile plants by applying a herbicide to the plants generated from crossing male-sterile plants with pollen from male fertile plants. Only the male sterile plants will survive.

Another way to utilize the components of this system in a recombinant DNA construct used to transform a plant is to embed an operator capable of controlling expression of a DNA sequence (e.g., a lexA operator), in a tissue specific promoter (e.g., the anther-specific promoter 5126); the tissue-specific promoter operatively linked to a DNA sequence that produces a gene product which inhibits pollen formation or function, e.g., a dominant negative gene such as DAM-methylase. To embed such an operator includes placing it (according to methods known to one skilled in the art) within, upstream or downstream of the nucleotide sequence of the promoters of the invention.

To reverse this effect, a plant transformed with such a construct is mated with a second plant that contains a second construct comprising the 5126 or other suitable promoter, including other anther-specific promoters such as the 5126 deletion mutation promoters or constitutive promoters, controlling the expression of a gene encoding a DNA-binding protein, e.g., the lexA gene which expresses the DNA binding protein lexA, which is capable of binding to the operator of the first construct. Specifically, the DNA-binding protein binds to the operator of the first construct and represses expression, thus shutting off expression of the DNA encoding a gene product which inhibits the function or formation of pollen and rendering a plant having both a first and a second genetic construct, male-fertile.

In a specific embodiment, LexA repressor protein produced by the second construct binds to the lexA operator embedded in the 5126 promoter in the first construct and, as a consequence of binding to this region of DNA, shuts off expression of the gene which inhibits pollen formation or function, e.g., a dominant negative gene such as DAM-methylase, and renders the transformed plant male-fertile.

When a construct of the present invention is linked with a selectable marker gene such as a herbicide resistance gene, the resulting construct enables a method to destroy segregating male fertile plants by applying a herbicide to the plants generated from crossing male-sterile plants with pollen from male fertile plants. Only the male sterile plants will survive.

According to another embodiment of the present invention, a genetic construct that has a methylase gene as the dominant negative gene operably linked to a tissue-specific promoter, such as the anther-specific 5126 promoter, is suitable for the practice of the present invention. A method for altering the development of a plant represents an aspect of the present invention. Such a method preferably comprises the steps of:

(a) transforming a plant with a genetic construct comprising a methylase gene and a suitable promoter; and (b) growing the plant in an environment in which the methylase gene is expressed, thereby altering expression of a gene, or genes, essential for a developmental process by methylating its promoter. To produce a male-sterile plant, the promoter allows gene expression only in a specific tissue, preferably a tissue critical for pollen formation or function, such as in the tapetum, in the anther or in early microspores. The construct may also include a methylase gene as the DNA sequence encoding a gene product capable of inhibiting pollen formation or function. A suitable methylase gene is a bacterial DAM (DNA adenine methylating) gene. Bacterial sources include E. coli. The DAM class of genes methylates a N6 position of adenine in the nucleotide sequence GATC. The construct includes a target DNA and is dominant negative because it represses the synthesis of mRNA by the target DNA.

A tissue-specific promoter is a promoter capable of controlling expression of a DNA sequence, for example a gene, in a specific tissue. For causing reversible male sterility in plants, promoters that are active in tissues directly or indirectly affecting pollen structure and/or function, are particularly suitable.

The search for tissue-specific promoters benefitted from the novel concept in plant genetics, of subtracting mutant from normal plant mRNA to result in mRNA differing from the normal in areas of the genome specifically related to the functions of interest in the present invention, anther development. An embodiment suitable for the present invention is an anther specific promoter, for example, the active DNA sequences of the novel plant promoter designated 5126.

Methods and compositions are described below for the production of male-sterile lines by the use of genetic constructs that include a methylase gene and a suitable promoter.

To correlate the insertion of a genetic construct of the present invention into a plant nuclear genome, with the male sterile phenotype of the plant, Southern blots of DNA of plants were analyzed. By this analysis, male sterility was found to be correlated with the presence of a genetic construct of the present invention.

In an embodiment of the invention, in order to destroy segregating male fertile plants so they do not grow in a field, a constitutive promoter is linked to a selectable marker and introduced into a plant with a genetic construct comprising a methylation gene regulated by a promoter. This system is useful when maintaining a sterile inbred line wherein a male fertile inbred plant is bred to a male-sterile plant of the same type. Seed harvested from the female male-sterile plant will segregate 1:1 for resistance to a selective agent. The plants may be sprayed with the selective agent; consequently, only the plants that have maintained the selectable marker gene survive. These plants are those that were transformed with the methylating construct.

The present invention also relates a male-sterile plant produced by methods of the present invention, and to the seed of such plants.

BRIEF DESCRIPTION OF THE DRAWINGS

FIG. 1 (SEQ ID No:1) lists a nucleotide sequence comprising the region upstream from the coding region of the genomic clone for 5126, the nucleotide sequence containing sequences of the promoter elements of the 5126 promoter. The coding sequence for clone 5126 begins with the ATG start codon at position 1488.

FIG. 18 (SEQ ID No:23) lists the DNA sequence of the 5126 cDNA. The putative start of translation of the cDNA sequence is at nucleotide position 73.

DETAILED DESCRIPTION OF PREFERRED EMBODIMENTS

Figure 2:
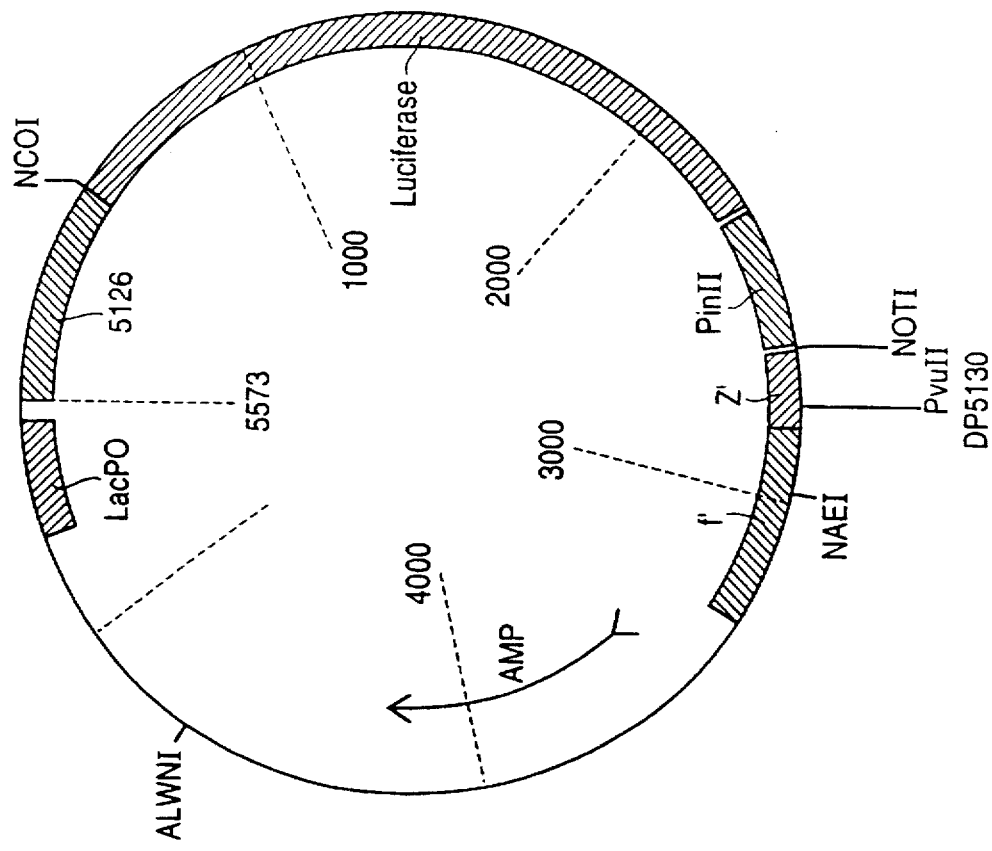
FIG. 2 presents a map of the DP5130 plasmid showing the NheI deletion of the maize 5126 promoter fused to the firefly luciferase gene.

The present invention relates the use of a genetic construct which includes a transcriptional activator and gene capable of acting on a DNA binding site to activate a dominant negative gene, a dominant negative gene, and suitable promoters, including a tissue-specific promoter controlling a gene acting on a DNA binding site, to affect plant development, for example, to cause male sterility. In transgenic plants, suitable dominant negative genes include cytotoxin genes, methylase genes, growth-inhibiting genes. Dominant negative genes include diphtheria toxin A-chain gene (Czako and An, 1991), cell cycle division mutants such as CDC in maize (Colasanti et al., 1991) the WT gene (Farmer et al., 1994) and P68 (Chen et al., 1991). In an illustrative embodiment, the DAM-methylase gene, the expression product of which catalyzes methylation of adenine residues in the DNA of the plant, is used. Methylated adenines will not affect cell viability and will be found only in the tissues in which the DAM-methylase gene is expressed, because such methylated residues are not found endogenously in plant DNA. A suitable system for DNA binding is the lexA-C1 system. Generally, the construct is exogenous and includes suitable promoters.

Altering development is particularly useful to produce a male-sterile plant. A method for producing a male-sterile plant is to transform a plant cell with a recombinant molecule (genetic construct) comprising the sense gene for the methylase protein. An appropriate promoter is selected depending on the strategy for developmental control. For example, a strategy is to express the methylase gene selectively in anther tissue by using an anther specific promoter. To produce a male-sterile plant, the transformed cell would be regenerated into a plant, pursuant to conventional methodology (see Materials and Methods).

In another embodiment of the present invention, a male-sterile plant is produced by placing a methylase gene under control of a promoter that is expressed selectively in cells critical to pollen formation and/or function. "Exogenous" used herein denotes some item that is foreign to its surroundings, and in particular applies here to a class of genetic constructs that is not found in the normal genetic complement of the host plant or is expressed at greater levels than in the endogenous state.

A "suitable promoter" includes a tissue-specific or cell-specific promoter that controls gene expression in cells that are critical for the formation or function of pollen, including tapetal cells, pollen mother cells, and early microspores.

In an embodiment designed to affect cells selectively that are critical to pollen development or function, a promoter that regulates gene expression in a specific cell or tissue, such as a tapetal cell, is used to control a gene encoding a DNA binding protein or a methylation sense gene.

A suitable promoter in this context is a tissue-specific regulatory element that effects expression only in tapetal tissue. Among such suitable promoters is the aforementioned 5126 promoter, derived from the 5126 clone, which restricts expression of a DNA sequence to anther tissue. The 5126 promoter includes nucleotide sequences upstream from the coding region of the genomic clone for 5126, as shown in FIG. 1, which are capable of controlling or regulating expression of a DNA sequence in anther tissue. Deletion mutants of the 5126 promoter, such as those characterized in Section (B) infra, are also suitable for use in the present invention in addition to specific regions of the 5126 promoter nucleotide sequence which exhibit the desired selective expression in anther tissue. Such specific regions of the 5126 promoter have been characterized and are set forth in Section (B) infra. Other suitable promoters include G9, SGB6, and TA39. Details of isolation and use of TA39 promoters are presented in the materials and methods section herein.

For the present invention, the condition of "male sterility in a plant" means 100% sterility, with no viable pollen shed. The condition can be ascertained by methodology well known to those skilled in the art, including such methods as determining pollen shed and germination tests.

An "anther-specific promoter" is a DNA sequence that directs a higher level of transcription of an associated gene in anther tissue than in some or all other tissues of a plant. Preferably, the promoter only directs expression in anthers. For example, the 5126 promoter is expressed in anther cells. The anther-specific promoter of a gene directs the expression of a gene in anther tissue but not in other tissues, such as root and coleoptile. Promoters of this specificity are described for example, in published European application 93810455.1, the contents of which are hereby incorporated by reference.

An "operator" (or "DNA binding site") is a DNA molecule that is located toward the 5' end of a structural gene and that contains a nucleotide sequence which is recognized and bound by a DNA binding protein that has either activation or repression function. The binding of a repressor protein with its cognate operator results in the inhibition of the transcription of the structural gene. For example, the lexA gene encodes a repressor protein that binds to the lexA operator.

An "isolated DNA molecule" is a fragment of DNA that is not integrated in the genomic DNA of an organism. Isolated DNA molecules may be chemically-synthesized.

The term "expression" refers to the biosynthesis of a gene product. For example, in the case of a structural gene, expression involves transcription of the structural gene into mRNA and the translation of mRNA into one or more polypeptides.

A "cloning vector" is a DNA molecule, such as a plasmid, cosmid, or bacteriophage, that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance.

An "expression vector" is a DNA molecule comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements.

The following examples are set forth as representative of specific and preferred embodiments of the present invention. These examples are not to be construed as limiting the scope of the invention in any manner. It should be understood that many variations and modifications can be made while remaining within the spirit and scope of the invention.

EXAMPLE 1.

Isolation and Characterization of the 5126 Promoter
(A) METHODOLOGY

Methods used for isolation of an anther specific promoter were novel for maize. The subtraction method of gene isolation only was useful after determination of the time in development that a suitable anther specific gene would be expressed, so that mRNA could be collected before and after that development threshold, to isolate a suitable gene.

Extensive comparisons of development of anthers from male-fertile maize with anthers from male-sterile maize suggested that anther mRNA subtraction at a time just before microspore degeneration would yield unique, anther-specific mRNAs. Total RNA was isolated from anthers from male-sterile plants just before microspore breakdown. With the dominant male-sterile mutant Ms44, this meant collecting anthers that were on or about the quartet stage of microsporogenesis. Anthers from fertile sibling plants also were collected at this stage. Male fertile and male sterile plants were collected as a source of mRNA.

(1) RNA Isolation: was performed by the guanidine isothiocyanate method known to those of skill in the art.

(2) mRNA Isolation: was accomplished by means of an oligo dT column by Invitrogen.

(3) cDNA Library construction: Libraries were made from tassel mRNA from maize stocks of a dominant male sterile mutation (Ms44) and its male fertile sibs (ms44) (available from Maize Stock Center, University of Illinois). The libraries were made by Invitrogen who used the bi-directional cloning method with the PCD-NAII vector and cloning at BstXI sites.

(4) Subtraction: Subtraction was done as described in the "The Subtractor I" instruction manual from Invitrogen version 2.3, using labelled cDNA from the male sterile dominant library as the driver, and unlabelled male fertile library as the tester (See Materials and Methods). This new library was labelled #5 and was expected to contain unique male fertile cDNA's.

(5) Unique Clones: Clones were isolated randomly from library #5 and inserts were gel purified and random hexamer labelled with P32 as well as slot blotted onto nitrocellulose. Duplicate clones were avoided by cross-hybridization. 5126 was one clone selected from the subtracted library #5. It was hybridized with non-tassel cDNA to ensure anther specificity of the clone.

(6) Full-Length cDNA Isolation: To obtain a full length 5126 cDNA a partial 5126 cDNA clone was isolated and sequenced using the m13 universal primer 5'TGTAAAACGACGGCCAGT 3' (M13 UP)(SEQ ID No:2) and the m13 reverse primer 5'CAGGAAA-CAGCTATGACC 3' (M13 RP)(SEQ ID No:3. This partial 5126 cDNA clone contains an insert of 594 bases which includes a polyA+ tail of 27 nucleotides. Total RNA and mRNA were isolated for library construction. The cDNA library was made by Stratagene using the Uni-Zap XR directional cloning system (EcoRI to XhoI). $1 \times 10^6$ PFU were screened with an EagI fragment from the partial 5126 cDNA to obtain a full length 5126 cDNA. ER1647 (NEB) was used as the host bacterium. Ten positive clones were purified to homogeneity. Plasmids were made by in vivo excision of the pBluescript SK(−) phagemid from the Uni-Zap XR vector (Stratagene Lambda Zap Instruction Manual, page 14). Sequencing was done by United States Biochemical Company on clone p5126-5; the sequence is set forth in FIG. 18. Both strands were entirely sequenced and agreed with the sequence of the partial cDNA. A Northern blot was done with the partial cDNA which indicated a transcript length of about 1.5 Kb. p5126-5 has a length of 1.485 Kb, which indicates it represents a full or nearly full length cDNA.

(7) Genomic Isolation: A genomic library was constructed from maize inbred line B73 DNA was partially digested with Sau3Al and cloned into the BamHI site of λ DASH II (Stratagene). 1×10⁶ PFU were screened with an EagI fragment from the partial 5126 cDNA. ER1647 (NEB) was used as the host bacterium. Three clones were isolated to homogeneity after three rounds of screening. DNA from these λ clones was isolated using a method reported by Bellomy and Record, (1989) and restriction sites were mapped. All three clones were identical, spanning approximately 18 Kb.

(B) CHARACTERIZATION OF PROMOTER 5126

(1) Northern analysis:

An EagI fragment derived from the partial 5126 cDNA was used to probe a Northern membrane containing maize polyA+ mRNA from etiolated leaves, roots, and green leaves from 6 day old seedlings, tassels with premeiotic stage anthers, tassels with meiotic stage anthers, tassels with quartet through uninucleate microspore stage anthers and ear shoots. The EagI fragment was labeled with horseradish peroxidase using the Enhanced Chemiluminescence (ECL) system from Amersham. Hybridization of the probe and membrane washes followed the manufacturer's protocol the ECL system. The cDNA probe hybridized to transcripts approximately 1.6 kb, present only in mRNA from tassels with quartet through uninucleate microspore stage anthers.

(2) Sequence analysis:

Three genomic clones in lambda DASHII which hybridized to the 5126 cDNA probe were isolated. These clones are 5125.4, 5126.5 and 5126.8.

From one of the genomic clones, 5126.8, a HindIII fragment of approximately 5 kb was isolated and subcloned into the HindIII site of the vector, BluscriptII KS+ (Stratagene). Two plasmids, DP4769 and DP4770, were generated containing the HindIII fragment inserted in two different orientations. The plasmids DP4769 and DP4770 were partially sequenced for one strand using the m13 universal primer, m13 reverse primer and with the oligonucleotide 5'CCTTCATCAGCTTCTGGCAG 3' (DO776) (SEQ ID NO:4). The sequence of DO776 was derived from the sequence of the 5' portion of the 5126 cDNA insert. A double strand sequence of DP4770 was obtained by "primer walking" with the following oligonucleotides, (SEQ ID NOS:5-8, respectively) 5'AGATCTCGGCCAGGCCCTTG 3' (D0990), 5'GAGTTGATGAAGTGA 3' (CWG4770), 5'GAGATCAATCAGCTAGAGG 3' (PG2-2), and 5'TAAACCTAAGGCC 3' (PG2-3). The sequence of DP4770 from the HindIII site to the region immediately adjacent to the D0990 sequence is 1594 bases.

A SacI fragment of approximately 6 kb long was isolated from the genomic clone 5126.8 and inserted into the SacI site of the vector BluscriptII KS+ (Stratagene). Two plasmids, DP5053 and DP5054, were generated with the SacI fragment inserted in two different orientations. The SacI fragment overlaps by 1207 base pairs with the HindIII fragment used for DP4769 and DP4770. This overlap is 5' of the region of DP4769 and DP4770 with homology to the cDNA insert of 5126. The sequence of 2106 bases for DP5053 was obtained by primer walking with the same oligonucleotides used for sequencing DP4770 and also with oligonucleotide 5'AATAGCCTAATTTATTAG 3' (PG2-4), oligonucleotide 5'ACATGTTTCAAGTTCAA 3' (PG2-5), oligonucleotide 5'CTTGTCAGAAGTTGTC 3' (PG2-5C) and oligonucleotide 5'CAACCATTACCGATGAA 3' (PG2-6C)(SEQ ID NOS 9-12, respectively).

5'RACE was used to obtain additional coding sequences for the 5126 gene. 5'RACE primer extension was performed using the 5'RACE system (Gibco BRL) with the oligonucleotide 5'ACGAGCGGACGCACGACAG 3' (DO1168)(SEQ ID No:13), derived from the sequence of DP4770, for primer extension with polyA RNA from maize tassels. The nested primer 5'TCCGTCGCCATCTGCGTCAC 3'(SEQ ID No:14), also from the DP4770 sequence, and the anchor primer 5° CACGCGTCGACTAGTACGGGIIGGGI-IGGGIIG 3' (SEQ ID No:15)(DO805) (modified from the anchor primer included in the 5'RACE system) were used for PCR amplification with TaqI DNA polymerase (Perkin Elmer). The 5' RACE product was subcloned into the pT7Blue(R) vector (obtained from Novagen). A clone containing the PCR product was named CGR3B. This plasmid was sequenced using DO805, DO1398 and m13 universal primers. The 5'RACE PCR insert is 412 bases long. There are polymorphisms between the near full length cDNA of the new A632 library, compared to the genomic clone from the B73 library and the original clone.

The sequence from CGR3B matches 586 bases of DP4770 with a 123 base intron present in the genomic sequence. The intron contains the highly conserved intron splice site motifs (5' GT and 3' AG). A putative start codon is seen which is in frame with the rest of sequence. This start codon has a reasonable start codon motif (CGATGG). Immediately upstream of this putative start codon, the sequence of CGR3B is relatively AT rich which is characteristic of 5'-untranslated cDNA sequences. There are 90 nucleotides in CGR3B upstream of the putative start codon which is a reasonable length for 5 ' untranslated regions in plants. In addition, the 5' most end of the CGR3B sequence homology in DP4770 is 35 bases downstream of a reasonable TATA box (TATATA). The 5126-5 sequence overlaps the sequence of CG3RB, with CGR3B having an additional 43 bases upstream.

This size correlates reasonably well with the transcript size estimated from northern hybridization of approximately 1.6kb.

(3) Site-directed mutagenesis

Site directed mutagenesis (Su and El-Gewely, 1988) was used to create an NcoI site in DP5053 at the putative translational start codon with the oligonucleotide 5'GCT-GCTCACCATGGCAAAGCAAC 3' (DO1398)(SEQ ID No:16) to create DP5055.

(4) Reporter constructs

A ScaI-NcoI fragment of approximately 4 kb, 5' of the 5126 coding region, was isolated from DP5055 and combined with a SmaI-NcoI fragment of DP1672 which contains the vector, the firefly luciferase region and the untranslated region of the proteinase II gene (pinII), to make the reporter construct DP5062. Deletions into the 5' end of the 5126 promoter fragment of DP5062 were prepared by removing sequences from the HindIII site in the polycloning region to the HindIII site 587 bases upstream of the ATG start condon (DP5121), or removing the sequence from the PstI site in the polycloning region to the PstI site 170 bases upstream of the ATG start codon (DP5122). Additional deletions from the 5'-end of the promoter fragment were generated by making use of the SphI site 855bp upstream of the translational start codon, the NdeI site 503 bp upstream of the start codon, or the KpnI site 216 bp upstream of the start codon. DO5062 was digested with SphI or NdeI, blunted with T4 DNA polymerase, and digested with NcoI after inactivating the polymerase. The resulting promoter fragments were cloned to the SmaI/NcoI fragment of DP1672, containing the vector of the luciferase reporter fused to the PinII 3' region. This gave rise to DP5131 (SphI deletion) and DP5130 (NdeI deletion) (FIG. 2). The KpnI deletion (DP5164) was obtained by a three-piece ligation of (1) the KpnI/ClaI fragment containing the promoter/luciferase junction, (2) the ClaI/AlwNI luciferase/PinII-3'/vector fragment, and (3) the AlwNI/KpnI fragment of the remaining vector piece from DP5062.

(5) Transient assays

Figure 3:
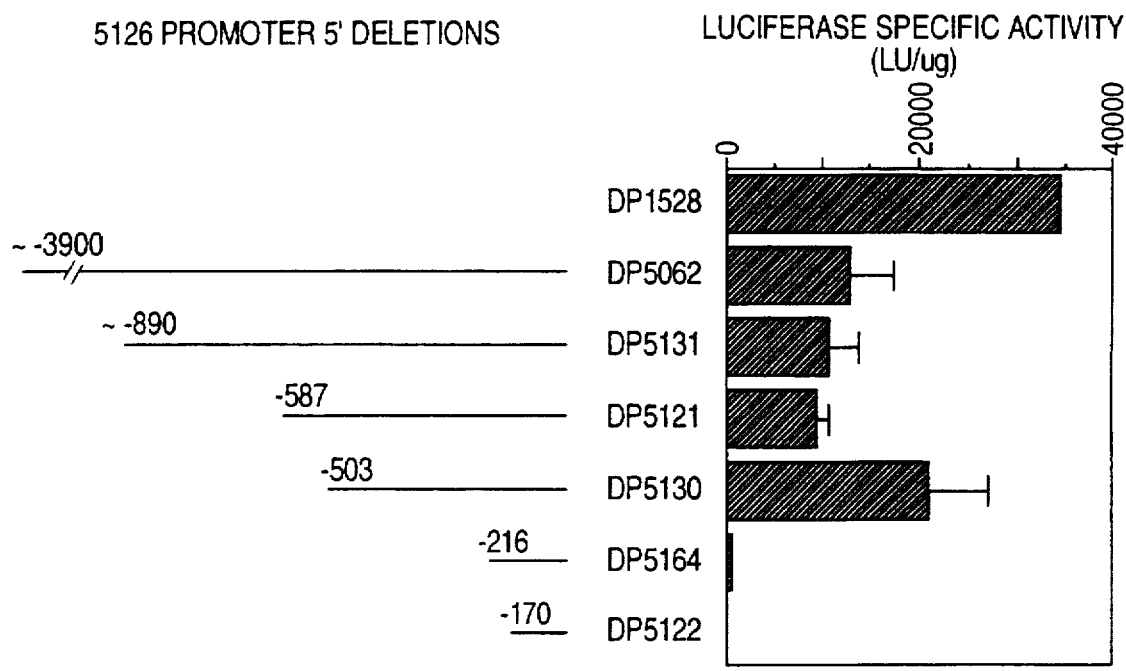
FIG. 3 sets forth the relative activity of P5126 deletions. Coordinates shown are relative to the translational start codon.

FIG. 3 shows the specific activity of luciferase obtained in anthers at the quartet to early uninucleate stage, when transformed with the full length 5126 promoter-luciferase construct (DP5062) or promoter deletion derivatives. Essentially full activity is observed in deletions up to the NdeI site 503 bp upstream of the translational start codon, but nearly all activity is lost upon deletion to the KpnI site 216 bp upstream of the start codon. No activity remains upon deletion to the PstI site 170 bp upstream of the start codon. Thus, a critical element is likely to occur between 170 and 503 bp upstream of the translational start codon.

Figure 4:
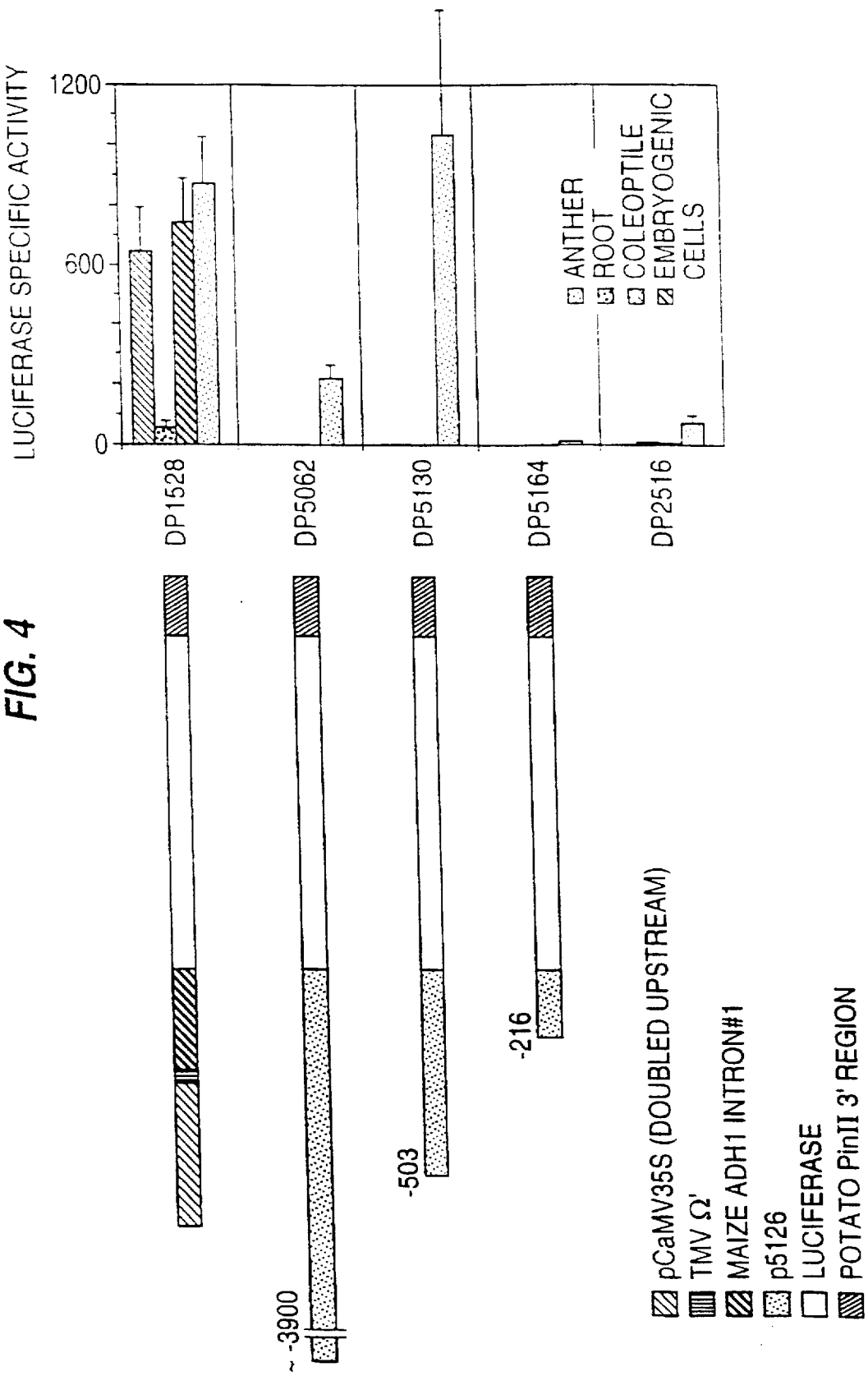
FIG. 4 provides information on tissue specificity of the 5126 promoter and deleted fragments of the promoter.

FIG. 4 shows the luciferase specific activity obtained in anthers, coleoptiles, roots and embryogenic suspension culture cells for the original 5126 promoter fragment reporter construct (DP5062) and the two key deletions (DP5130 and DP5164) compared to positive and tissue-specific controls (DP1528, containing a luciferase reporter gene driven by a "constitutive" CaMV 35S promoter, and DP2516, containing a luciferase reporter driven by an anther-specific promoter SGB6). Tissue-specificity, observed for the full-length promoter fragment, was maintained in the NdeI deletion.

Figure 5:
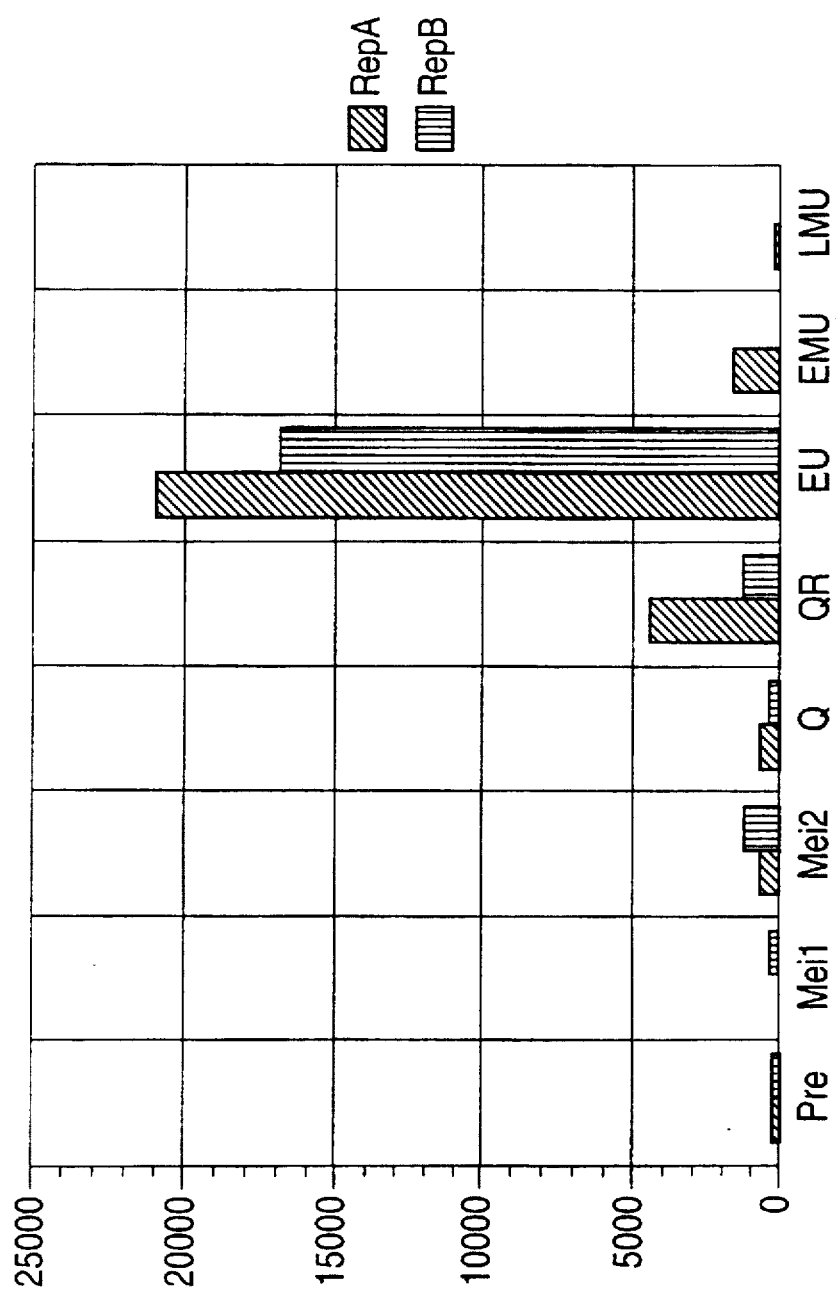
FIG. 5 is a graphical representation of stage specificity of the–503 P5126 deletion used in the DP5814 plasmid: Pre=Premeiotic; MeiI=Meiosis I; Mei2=Meiosis II; Q=Quartet; QR=Quartet Release; EU=Early Uninucleate; EMU=Early-Mid Uninucleate; LMU=Late-Mid Uninucleate.

FIG. 5 shows the timing of anther activity of the 5126(−503) promoter. This deletion promoter is most active in early uninucleate microspore stages, although activity spans meiotic stages through the mid-uninucleate microspore stage.

EXAMPLE 2.

Construction of DAM-methylase Plasmids

A DAM-methylase gene was obtained from *E. coli*. A methylase gene derived from any plant is also suitable.

Figure 6:
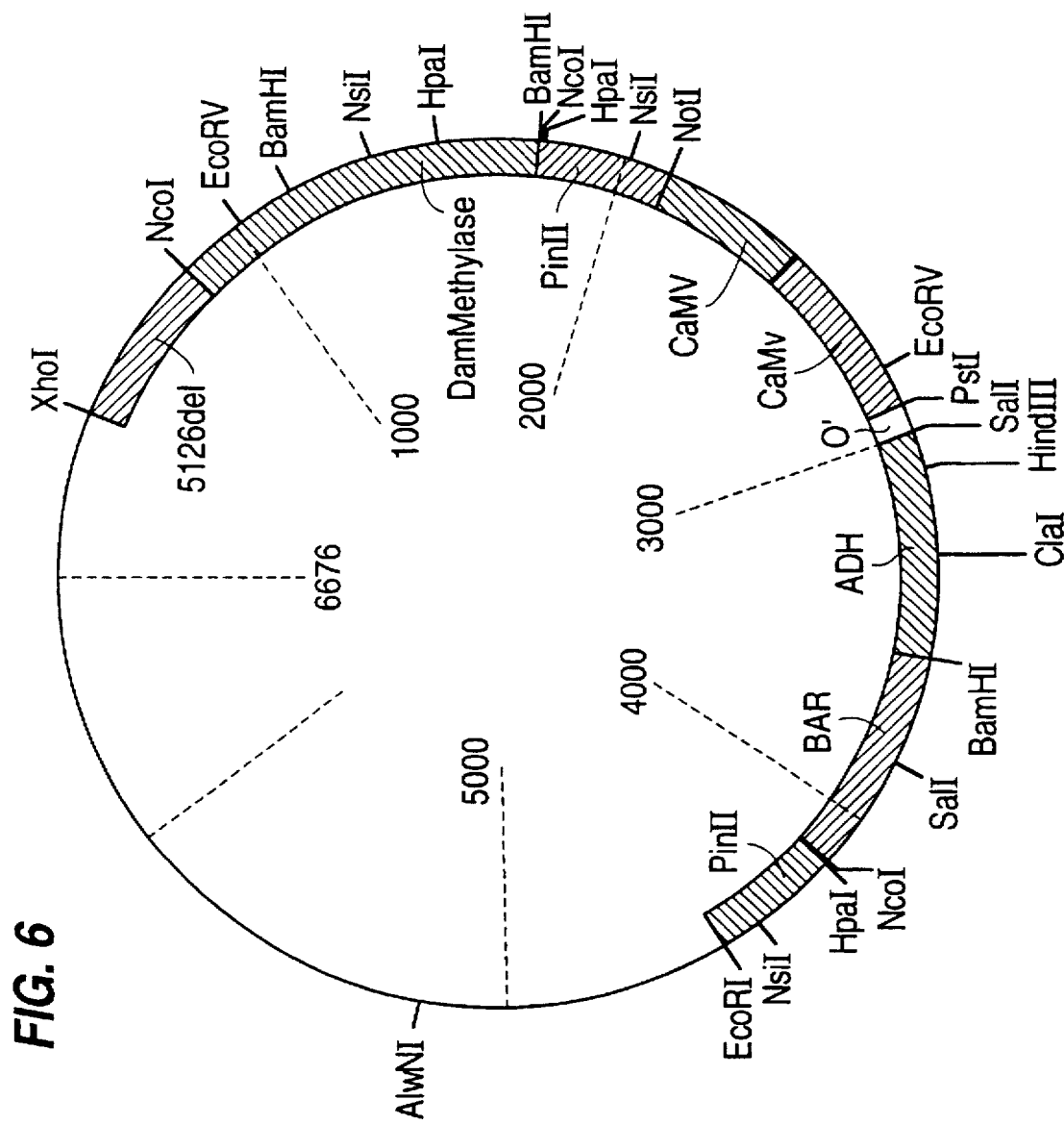
FIG. 6 presents a map of the DP5814 plasmid, which contains a 5126 deletion promoter fused to *E. coli* DAM methylase and also contains the double CaMV 35S promoter, ADHI intron fused to the gene BAR and pinII terminator.

The DAM-methylase gene (nucleotides 195-1132 from Brooks, et al., 1983) was modified by site-directed mutagenesis (Su and ElGewley, 1988) and a SmaI site was introduced at nucleotide 186, nine nucleotides 5' to the initiating codon ATG. DP5814 (FIG. 6) is a plasmid used in maize transformation which contains the anther-specific DAM-methylase gene in cis with a constitutively expressed BAR gene. This plasmid was constructed by ligating the 500 bp XhoI/NcoI fragment containing the NdeI-NcoI deletion of the 5126 anther-specific promoter region from DP5130 (FIG. 2) to a 1.0 kb SmaI/BamHI fragment containing the modified DAM-methylase sequences described above. The NcoI site contained on the XhoI/NcoI 5126 promoter fragment was filled in with dNTPs using T4 DNA polymerase (Boehringer-Mannheim) according to established protocols (Sambrook et al., 1989) to generate a blunt-end for cloning. The promoter/gene junction resulted in the addition of 3 N-terminal residues encoded by the following sequence (the initiating MET of the native DAM-methylase gene is underlined and corresponds to nucleotides 195-197 in Brooks et al., 1983):

5'CCATGGGGACAATG 3' (SEQ ID No:917)

The DAM-methylase expression is terminated by ligating the 320 bp BamHI-NotI fragment that contains the 3' PinII sequences from the potato proteinase inhibitor II gene (nucleotides 2–310, from An et al., 1989). This chimeric gene contained on a 1.6 kb XhoI-NotI DNA fragment was cloned into the XhoI-NotI restriction site in a monocot expression plasmid that contains the enhanced cauliflower mosaic virus 35S promoter (nucleotides −421 to +2, repeating −421 to −90 in tandem, Gardner et al., 1981), the tobacco mosaic virus (TMV) leader (79 bp HindIII-SalI fragment, as reported by Gallie et al., 1987), a 579-bp fragment containing the intron 1 from the Adh-S allele of the maize alcohol dehydrogenase gene (Dennis et al., 1984), the BAR gene which encodes for the enzyme phosphinothricin acetyltransferase (nucleotides 160–704 from Thompson et al., 1987, where the nucleotide 160 was changed from a G to an A to generate a MET initiation codon) and the termination sequences from the potato proteinase inhibitor II gene (nucleotides 2–310, from An et al., 1989), in a pBluescript (Stratagene) backbone.

EXAMPLE 3.

Production of a Male-Sterile Plant

Plants were transformed with DP5814. DP5814 contains the Nde1 deletion derivative of the 5126 promoter fused to the *E. coli* DAM-methylase gene and the PINII terminator. This plasmid also contains the double 355 cauliflower mosaic virus promoter fused to the BAR gene. (Thompson et al., 1987).

Figure 13:
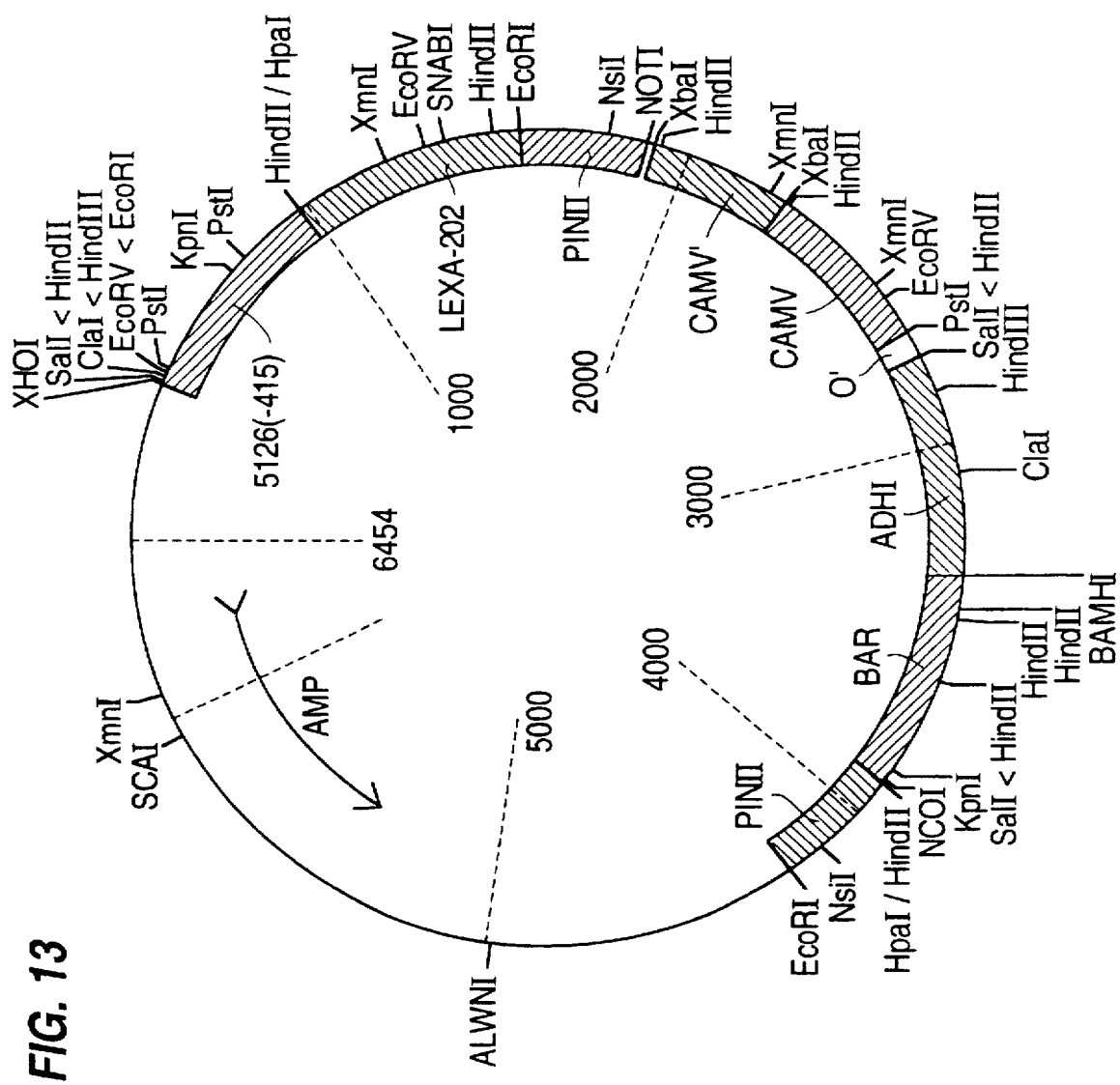
FIG. 13 presents a map of the PHP6522 plasmid which contains the 5126 deletion promoter fused to the *E. coli* lexA gene and also contains the double CaMV 35S promoter, maize ADH1 intron fused to the BAR gene and pinII terminator.

Construct PHP6522 (FIG. 13) is identical to that described for DP5814 with the exception that the coding sequences of the Dam methylase gene was replaced by the lexA coding region from amino acid 1 to 202 (Golemis, 1992).

Figure 14:
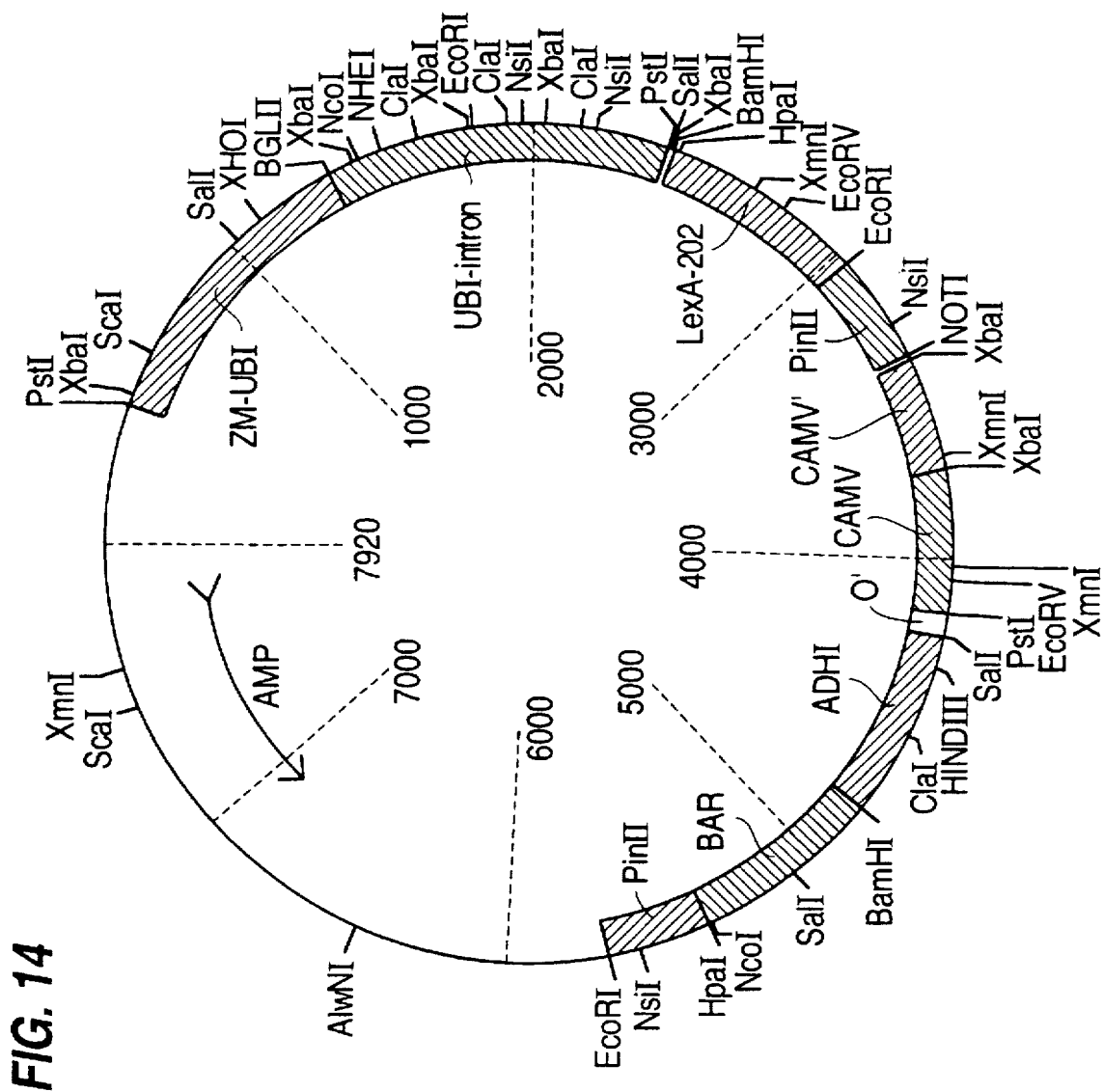
FIG. 14 presents a map of the PHP6555 plasmid which contains the maize ubiquitin promoter and intron fused to the *E. coli* lexA gene and also contains the double CaMV 35S promoter, maize ADH1 intron fused to the BAR gene and pinII terminator.

Construct PHP6555 (FIG. 14) is identical to that described for PHP6522 with the exception that the 5126 promoter was replaced by the maize ubiquitin promoter and intron which is contained on a 1.9 kB PstI DNA fragment.

DP5814 was bombarded into Hi Type II (B73×A188) (Armstrong, 1991) callus cell-lines from which Bialophos-resistant plants were regenerated. To serve as controls for male-fertility, untransformed plants were also generated. Transgenic and control calli were analyzed by PCR.

A transgenic plant containing a methylase gene construct can be regenerated from a culture transformed with that same construct, so long as the plant species involved and the type of culture used are susceptible to regeneration. "Culture" in this context comprehends an aggregate of cells, a callus, or derivatives thereof that are suitable for culture.

A plant is regenerated from a transformed cell or culture, or from an explant, by methods disclosed herein that are known to those of skill in the art. Methods vary according to the plant species. Seed is obtained from the regenerated plant or from a cross between the regenerated plant and a suitable plant of the same species using breeding methods known to those of skill in the art.

EXAMPLE 4.

Effect of 5126::DAM-Methylase on Fertility of Maize Plants

Regenerated maize plants transformed with the DP5814 construct were analyzed by PCR for the presence or absence of the DAM-methylase coding region and scored for their ability to generate fertile pollen.

The polymerase chain reaction (PCR), which is well-known to those of skill in the art, was used to determine the presence of the *E. coli* DAM-methylase gene. The oligonucleotides used were D01266 and D01267:

The oligonucleotides have the following sequences:

D01266 (SEQ ID NO: 18)
  5'-ATG AAG AAA AAT CGC GCT TTT TTG AAG TGG GC-3'

-continued

DO1267 (SEQ ID NO: 19)
5'-TCA CCC AGG CGG GCA AAA TCA GCC GAC A-3'

These oligos were employed as primers in PCR to amplify the E. coli DAM-methylase gene specifically.

Twenty-five independent primary transgenic maize plants that were PCR positive for the DAM-methylase gene were analyzed. Twenty-two of these DAM-methylase PCR positive plants were male-sterile. Southern analysis conducted on these plants detected the presence of single-copy to multiple copy insertion events. Microscopic examination of pollen development in these male-sterile plants as compared to either PCR negative or untransformed plants revealed that premeiotic and meiotic microspores can be observed in all plants, however quartet microspores have not been observed in any of the anthers derived from plants that are PCR positive for the DAM-methylase gene and are male-sterile. This breakdown of microspore development is consistent with the observation that luciferase activity can first be detected at a similar stage of development when expressed under the control of the 5126NdeI deletion promoter, suggesting that expression of the DAM-methylase gene during early microspore development interferes with normal pollen formation.

Male-sterile maize plants were pollinated with pollen derived from untransformed maize plants, the seed was germinated and resulting plants were analyzed for cosegregation of herbicide resistant male-sterile plants with the presence of the 35S: Bar-5126:DAM-methylase construct to establish a correlation between the presence of the methylase gene and male-sterility. Southern analysis of T1 populations derived from 13 independent male-sterile T0 events has revealed that all of the male-sterile bialophos resistant plants contained the E. coli DAM-methylase and BAR genes whereas male fertile, bialophos sensitive segregants did not contain these genes.

Similar to the observations made in the T0 plants, microspore development breakdown occurred between meiosis I and quartet stages.

EXAMPLE 5.

Southern Blotting to Correlate the Male Sterile Phenotype in a Plant with the Insertion of a Genetic Construct Capable of Methylation Nine mls of CTAB extraction buffer (100 mM Tris pH 7.5), 1% Hexadecyl trimethyl-Ammonium bromide, 0.7M Sodium chloride, 10 mM EDTA) were added to 300 mg of lyophilized leaf tissue, vortexed and incubated at 65° C. for 1 hour. Five mls of a chloroform/octanol (24:1) solution were added and mixed for 5 minutes. Extracts were spun for 30 minutes at 2500 rpm. The top layer was removed and placed in a new tube, and 11 mls of CTAB precipitation buffer (same as CTAB extraction buffer minus the sodium chloride) were added, inverted and allowed to stand for 30 minutes. The sample was spun for 10 minutes at 2000 rpm. To resuspend the pellet, 2 mls of 100 mM Tris (pH 7.5), 10 mM EDTA, 0.7M NaCl were added and heated for 15 minutes at 60° C. 10 μl of RNAseA (10 mg/ml) were added and incubated for 30 minutes at 37° C. Five ml of cold 100% ETOH is added to the tube and mixed gently, the DNA is hooked out using a bent 9 inch Pasteur pipet, placed into a tube that contains 76% ETOH, 0.2M sodium acetate and allowed to sit for 20 minutes. The DNA is transferred to a new tube that contains 76% ETOH, 0.2M ammonium acetate for 1 minute, wiped dry and resuspended in 300 μl of TE (10 mM Tris |pH 7.5|, 1 mM EDTA). 5 μg of genomic DNA digested with restriction endonucleases was electrophoresed on 0.8% agarose gels containing Tris-acetate buffer; gel was prepared for transfer to the membrane by incubating for 20 minutes in 500 mls of 0.25M HCl, 40 minutes in 500 mls of 0.4M NaOH, 0.6M NaCl and 30 minutes in 0.5M Tris (pH 7.5), 1.5M NaCl. Transfer was done by using 25 mM sodium phosphate buffer, pH 6.5 onto Amersham Nylon FP membrane. After transfer, membrane was baked at 80° C. under vacuum. Prior to the first use of the membrane, it is incubated at 65° C. in a solution containing 0.1×SCP (1×SCP; 0.1M NaCl, 16 mM sodium phosphate, pH 7.0) and 0.1% SDS for 30 minutes. P32-dCTP labelled DNA probes were generated with a random primer-labelling kit supplied by Amersham according to the manufacturers instructions. To generate the DAM-methylase specific probe, the 635 bp BamHI DNA fragment was isolated from DP5814 and labelled. To generate a BAR-specific probe, a 560 bp NcoI-BamHI DNA fragment was isolated from DP5814 and labelled. The labelled probe was denatured for 10 minutes at 95° C., added to the filter in 20 mls of hybridization buffer (0.1XSCP containing 1.0× Dextran sulfate) and incubated at 65° C. overnight. The filter was washed 3 times with 0.1×SCP containing 0.1% SDS at 65° C. The filter was exposed to X-ray film with a screen (Dupont) at −70° C.

EXAMPLE 6.

Construction of Transient Assay Plasmids

Figure 7:
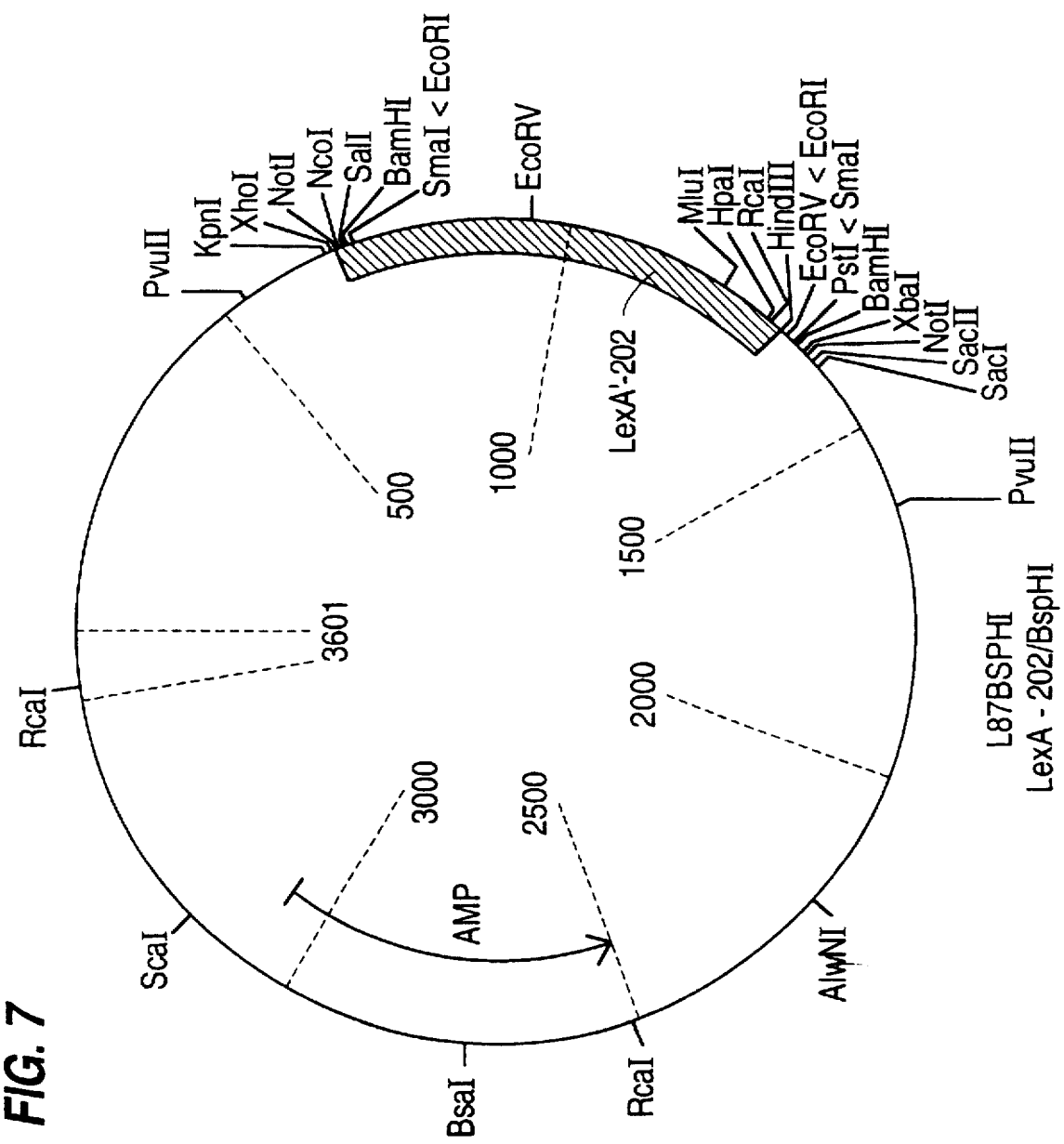
FIG. 7 presents a map of the L87BspHI plasmid including the *E. coli* lexA202 gene containing a mutagenized ATG codon within a novel BspHI restriction site.
Figure 8:
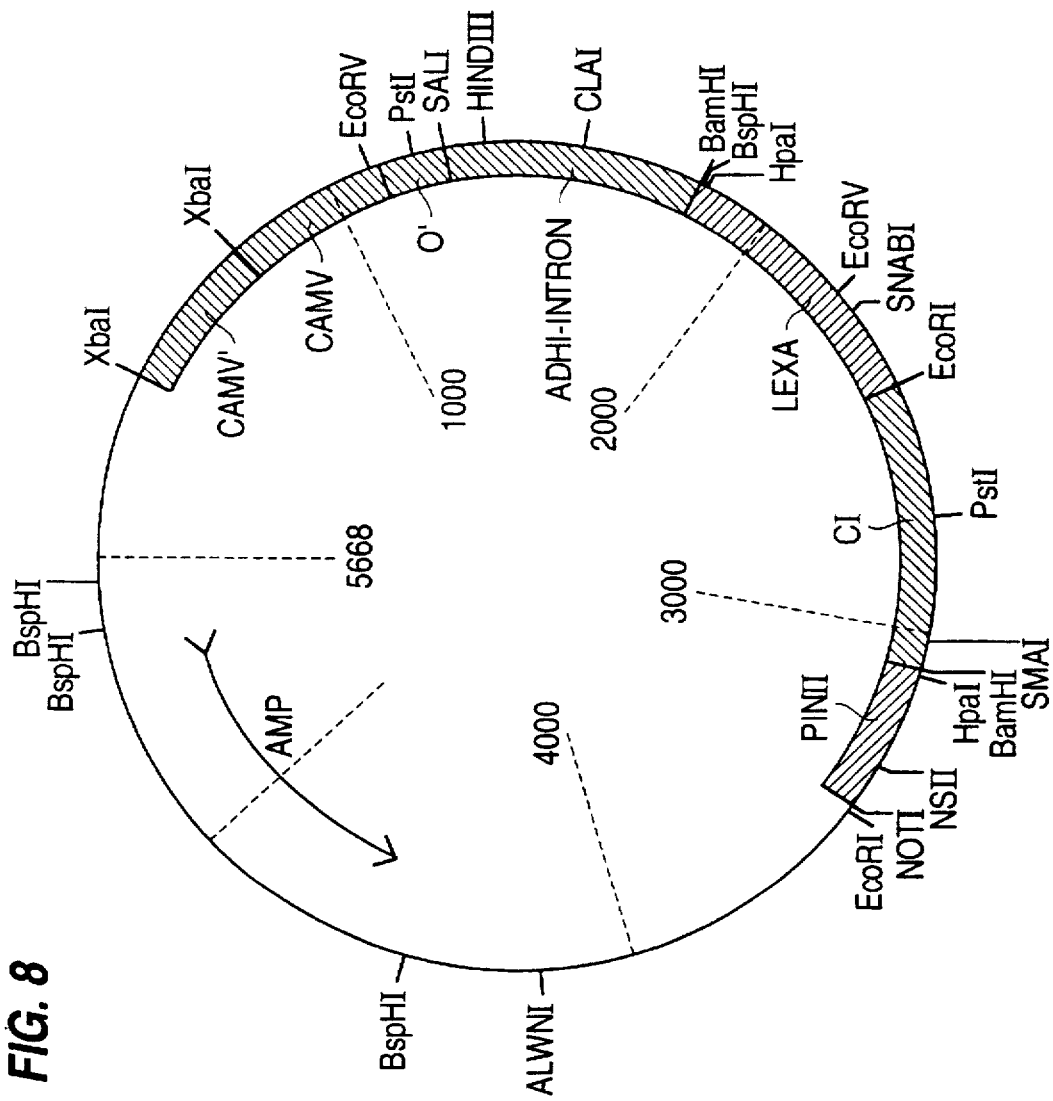
FIG. 8 presents a map of the L121 plasmid containing the double CaMV 35S promoter, ADH1 intron fused to the lexA202 maize C1 gene hybrid and pinII terminator.

A HindIII/XhoI fragment containing the LexA202 gene (nucleotides 734–1406 in pEG202 in Golemis and Brent, 1992) was cloned into pBluescriptSK+(Stratagene) to generate plasmid L87. Site-directed mutagenesis (Su and El Gewley, 1988) of this plasmid using the oligo DO2326 (SEQ ID No:20):

5' CCGTTAACGCTTTCATGACGCCCGGAATTAAGC 3' resulted in the introduction a BspHI site at the initiating ATG of the LexA-202 reading frame (nucleotide 754, Golemis and Brent, 1992) generating the plasmid L87BspHI (FIG. 7). A chimeric gene containing the LexA sequences encoding residues 1–202 on a BspHI/EcoRI fragment from L87BspHI was fused in-frame with an EcoRI/HpaI fragment residues 144–273 from the maize C1 described above into a monocot expression plasmid containing the enhanced cauliflower mosaic virus 35S promoter (nucleotides −421 to +2, repeating −421 to −90 in tandem, Gardner et al., 1981), the tobacco mosaic virus (TMV) leader (79 bp HindIII-SalI fragment, as reported by Gallie, et al., 1987), a 579-bp fragment containing the intron 1 from the Adh-S allele of the maize alcohol dehydrogenase gene (Dennis et al., 1984), and the termination sequences from the potato proteinase inhibitor II gene (nucleotides 2–310, from An et al., 1989), in a pBluescript backbone generating plasmid L121 (FIG. 8).

The construct DP5817 (FIG. 9) contains the enhanced CaMV promoter, TMV leader Adh intron and the PinII termination sequences described above. The sequences coding for residues 1–202 of the LexA protein carried on a BspHI/SmaI fragment from L87BspHI (nucleotides 754–1382 in pEG202 in Golemis and Brent, 1992) were cloned downstream of the Adh intron replacing the LexA-C1 chimeric gene found in L121.

Figure 10:
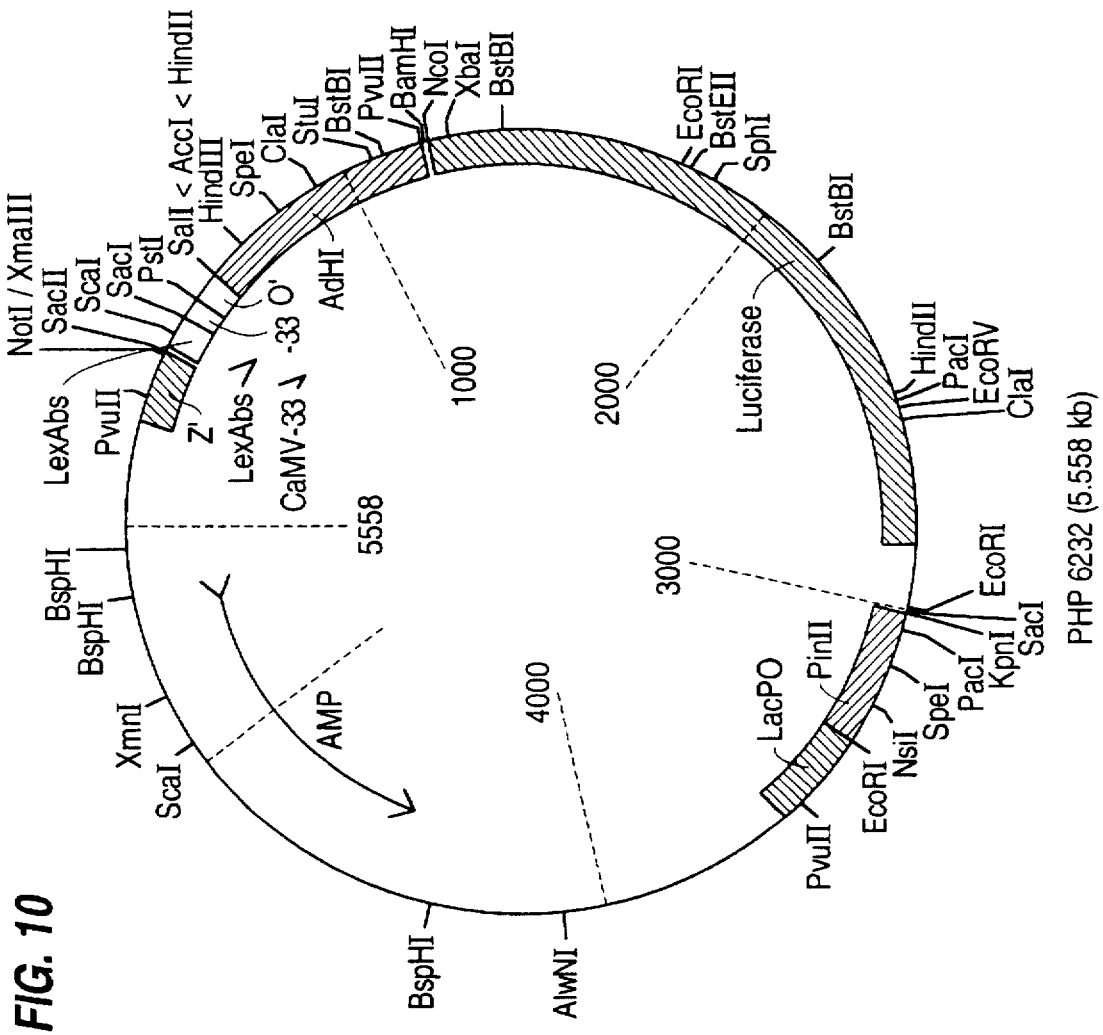
FIG. 10 presents a map of the DP6232 plasmid which contains a minimal CaMV 35S promoter (−33) containing lexA binding site, ADH1 intron, firefly luciferase and pinII terminator.

The reporter plasmid, DP6232 (FIG. 10) contains three tandemly repeated lexA DNA binding sites carried on the complementary oligonucleotides, DO2448 and DO2449, with the following nucleotide acid sequences. DO2448 (SEQ ID No:21)

5' GATCTACTGCTGTATATAAAACCAGTGGTTATATGTACA
GTACTGCTGTATATAAAACCAGTGGTTATATGTACAGTA
CGGATG 3'

D  O  2  4  4
3' ACGACATATATTTTGGTCACCAATATACATGTCATGACG 9  (SEQ ID NO: 22):
ACATATATTTTGGTCACCAATATACATGTCATGCCGATG 5'

The oligos were annealed and cloned as a BglII/NdeI fragment upstream of a truncated CaMV promoter (nucleotides −33 to +2; see Gardner et al., 1981), the TMV leader, ADH intron, the coding region of the firefly luciferase gene (+53 to +1708, dewet et al., 1987), and the PinII termination sequences in a pBluescript backbone.

Construct DP6509 (FIG. 11) is a plasmid containing three chimeric genes designed for expression in maize plants. The plasmid also contains the lexA binding sites upstream of a truncated CaMV promoter, the TMV leader and ADH intron and PinII terminator as described for DP6232 with the DAM-methylase gene, maintaining the 9 bp addition as described above in place of the luciferase coding sequences. The gene sequences encoding the anther-specific transcriptional activator 5126::LexA-C1 are located immediately downstream of the DAM-methylase reporter gene described above. This gene contains the XhoI/NcoI fragment carrying the 5126 promoter sequences from DP5130, the LexA202-C1 chimera and PinII sequences described for L121. The third gene encoded by this plasmid contains the enhanced CaMV promoter, TMV leader, Adh intron, BAR coding sequences and the PinII terminator on a pBluescript backbone as described for DP5814.

Figure 15:
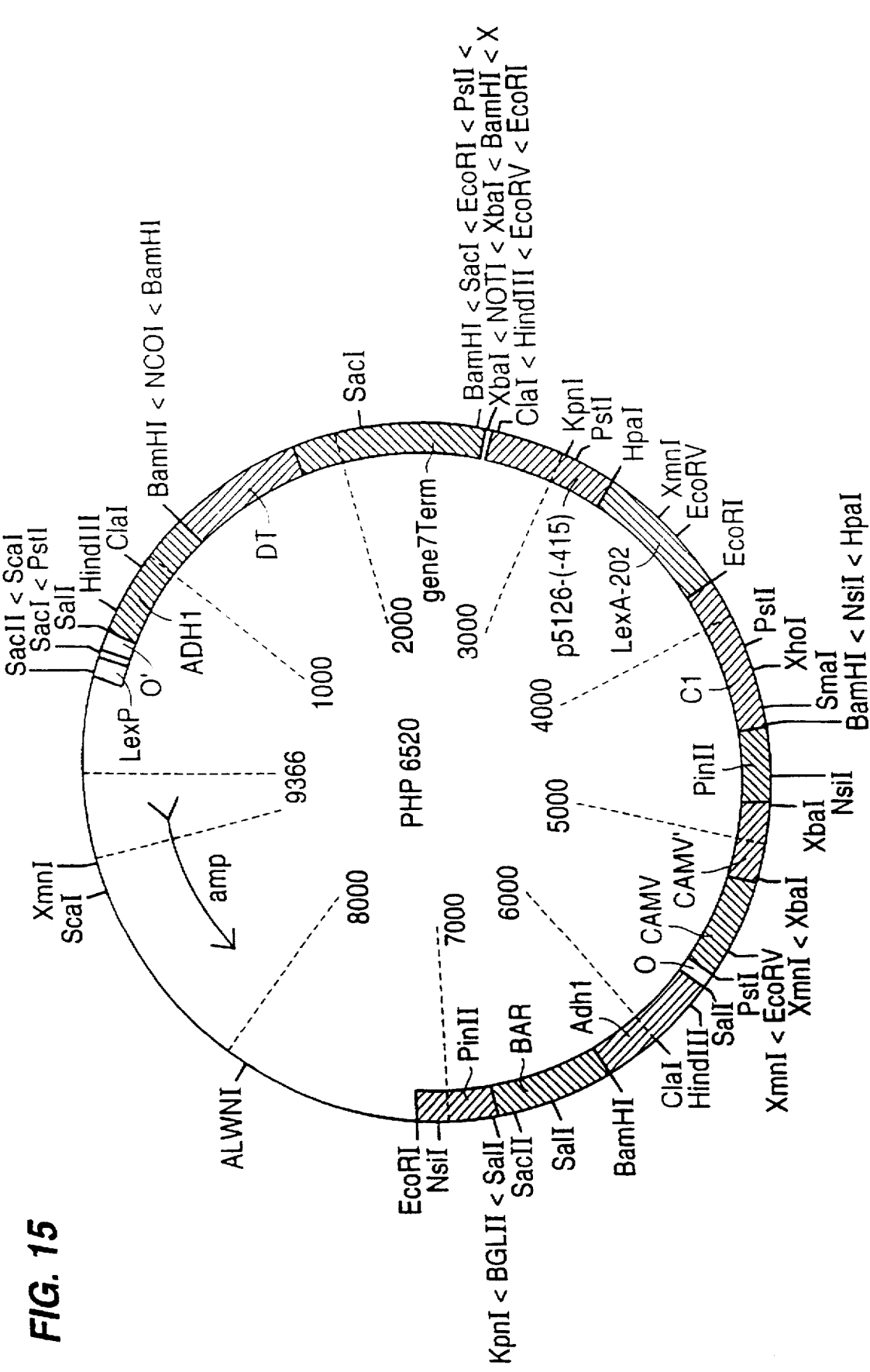
FIG. 15 presents a map of the PHP6520 plasmid which contains a lexA binding site with a minimal −33 CaMV promoter, Adh1 intron, cornynebacteriphage diphtheria toxin A subunit and gene 7 terminator, and which also contains the 5126 promoter fused to lexA202-c1 and the selectable marker construct CaMV 35S::BAR.

Construct PHP6520 (FIG. 15) is the same as that described for PHP6509 with the exception that the coding sequences of the Dam Methylase gene and pinII terminator were replaced by the diphtheria toxin coding region and gene 7 terminator (Czako and An, 1990).

Figure 16:
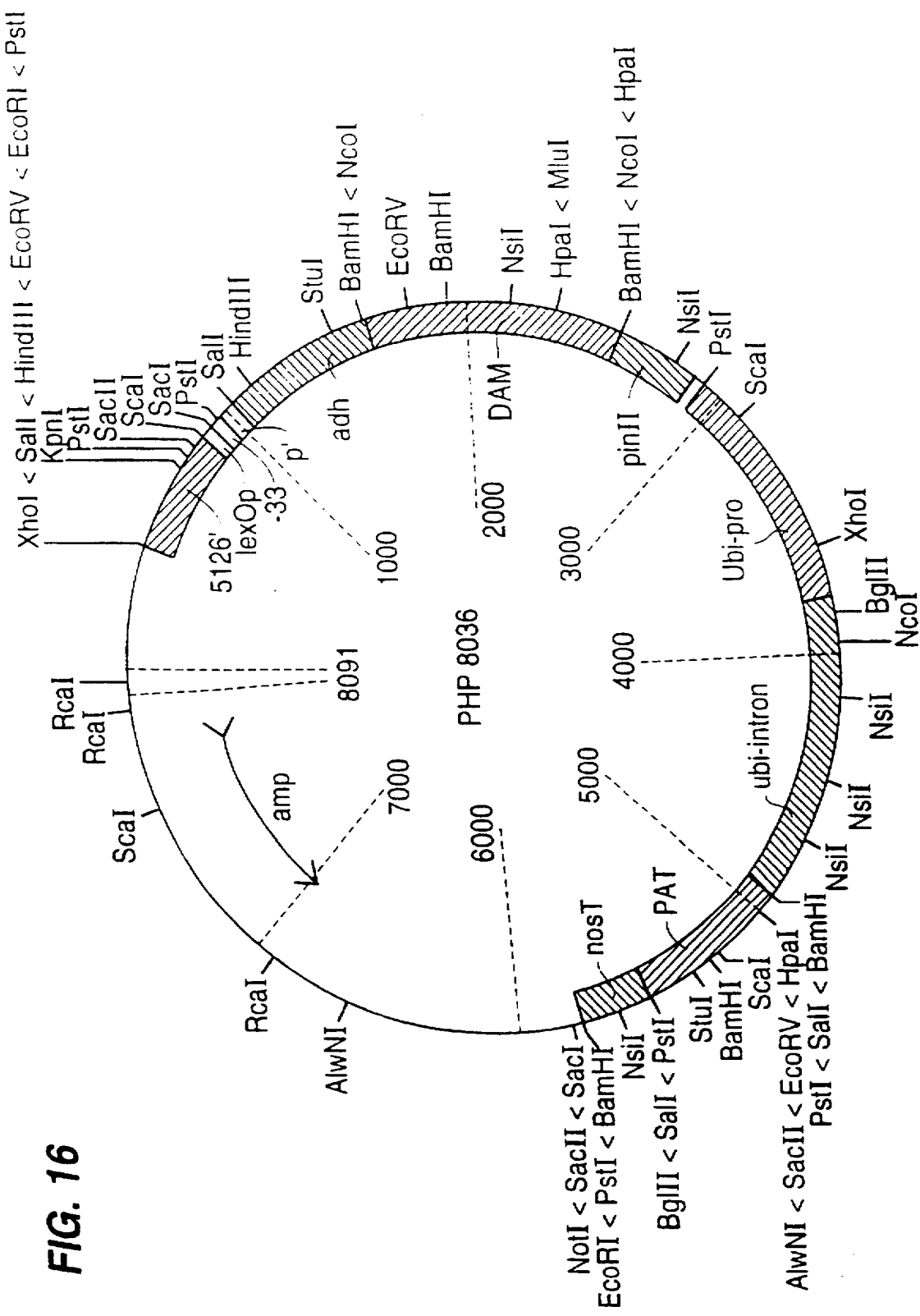
FIG. 16 presents a map of the PHP8036 plasmid which contains the 5126 deletion promoter, a lexA binding site with a minimal −33 CaMV promoter, Adh1 intron, *E. coli* Dam methylase and pinII terminator which also contains the selectable marker construct Ubiquitin:PAT.

Construct PHP8036 (FIG. 16) contains a the 5126 promoter from positions −503 to −134, fused to the lexA binding site upstream of the minimal −33 CaMv promoter, the TMV leader, ADH1 intron the coding region of Dam methylase and the pinII terminator as described for DP6509. The plasmid also contains the selectable marker construct Ubi-Pat, which was constructed by fusing a 1.9 kB maize ubiquitin promoter and intron to the modified phosphinothricin-N-acetyl-transferase gene (Pat) from Streptomyces viridochromagenes and the nopaline-synthetase gene (Droge, et al.).

Figure 17:
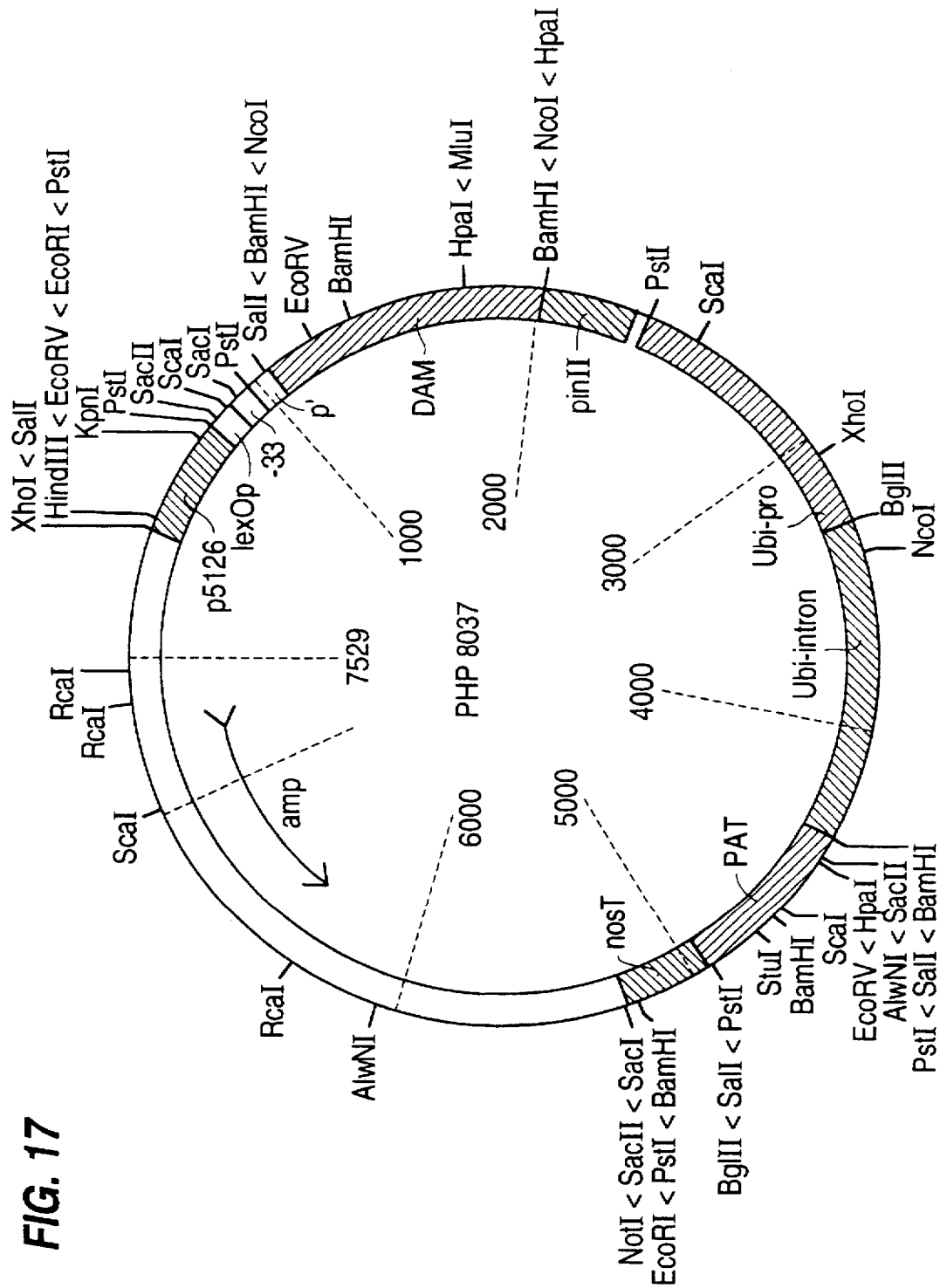
FIG. 17 presents a map of the PHP8037 plasmid which contains the 5126 deletion promoter, a lexA binding site with a minimal -33 CaMV promoter, *E. coli* Dam methylase and pinII terminator which also contains the selectable marker construct Ubiquitin:PAT.

Construct PHP8037 (FIG. 17) is identical to PHP8036 with the exception that the maize AdhI intron contained within the 650 bp SalI/BamHI DNA fragment was removed from the 5126:lexA:Dam methylase portion of the plasmid.

EXAMPLE 7.

Expression of a Luciferase Reporter Containing lexA Binding Site Upon Transient Co-Expression of Either lexA-C1, lexA or Both Experiments were conducted to address two questions. First, can the bacterial DNA binding protein lexA promote and enhance gene expression in plant cells? Second, does co-expression of the lexA protein with the transcriptional activator lexA-C1 result in the repression of activator-mediated gene expression.

The lexA protein would bind to a region of DNA containing the lexA DNA binding site ("lexA operator") but would not recruit the necessary plant derived transcriptional components to initiate mRNA synthesis. But it has been shown that juxtaposition of protein regions that can act as transcriptional activators to DNA binding proteins will result in increased expression of the reporter gene (Ruden et al., 1991). To test the ability of the lexA gene to promote expression of a reporter gene in maize cells, a region of the maize C1 gene (Goff et al., 1991) encoding a transcriptional activation domain was fused in-frame with the region of DNA that corresponds to the DNA binding protein lexA, to generate the hybrid gene, LexA202-C1. The hybrid gene was placed under the transcriptional control of the constitutive promoter 35S to generate plasmid L121 as shown in FIG. 8.

Figure 12:
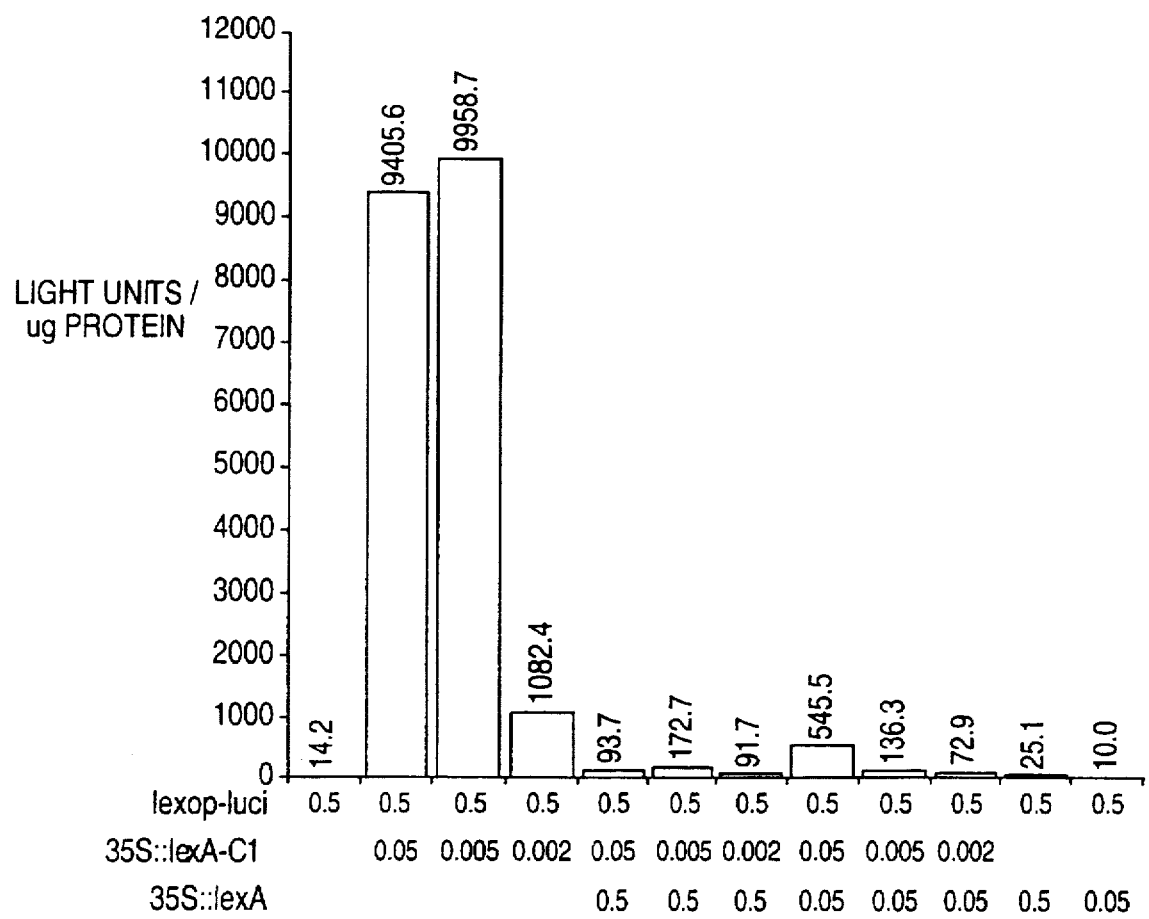
FIG. 12 is a bar graph illustrating lexA202-C1 activation and lexA mediated repression in maize embryogenic suspension cells, at varying DNA doses (the numbers shown identify relative amounts of DNA).

This construct was co-bombarded at varying amounts into maize embryogenic suspension cells with a constant amount of a luciferase reporter gene that contains the lexA binding site, plasmid DP6232. As shown in FIG. 12, the reporter alone yields very low luciferase activity (fourteen light units per microgram total protein (14 lu/µg), however high luciferase activity (>9000 lu/µg) is detected when the lexA-C1 transactivator is co-bombarded at amounts greater than 5 ng per shot.

Figure 9:
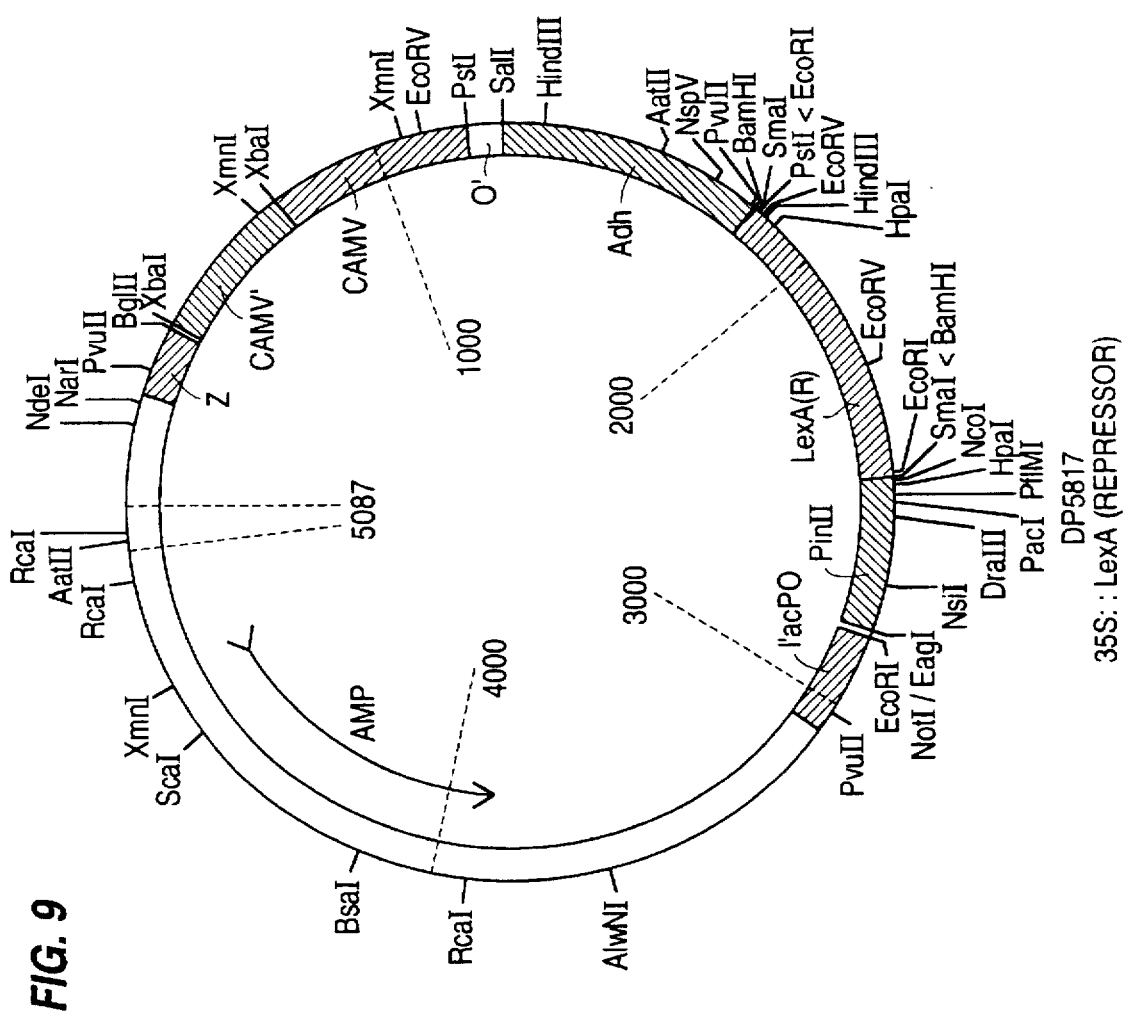
FIG. 9 presents a map of the DP5817 plasmid, containing the double CaMV 35S promoter, ADH1 intron fused to the lexA202 gene and pinII terminator.

To determine if the lexA protein will repress the high level of luciferase expression, the plasmid DP5817 which contains a 35S:lexA construct as shown in FIG. 9 was co-bombarded with DP6232 and L121, varying the amounts of L121 or DP5817. As shown in FIG. 12, addition of DP5817 to treatments containing the lexA-C1 construct and reporter results in reduced luciferase activity. Together these data suggest that in maize embryogenic suspension cells enhanced expression of a gene containing a lexA DNA binding site is detected when the lexA-C1 fusion protein is co-expressed and that this expression may be repressed by the lexA protein.

EXAMPLE 8.

Reversion to a Male-Fertile Plant

In accordance with the present invention, there are several strategies to produce reversion of a male-sterile to a male-fertile plant. A cascade effect wherein a promoter, such as the tapetal specific promoter 5126 is fused to the transcriptional activator LexA-C1 gene (herein called 5126::LEXA-C1) where the LexA portion of the gene encodes the bacterial LexA protein that binds to a region of DNA called the LexA operator (LexAop) and the C1 portion of the gene encodes the maize C1 protein that interacts with the maize transcriptional machinery to promote transcriptional activation of genes that contain the LexAop within the context of a minimal promoter element, for example the minimal 35S promoter.

Figure 11:
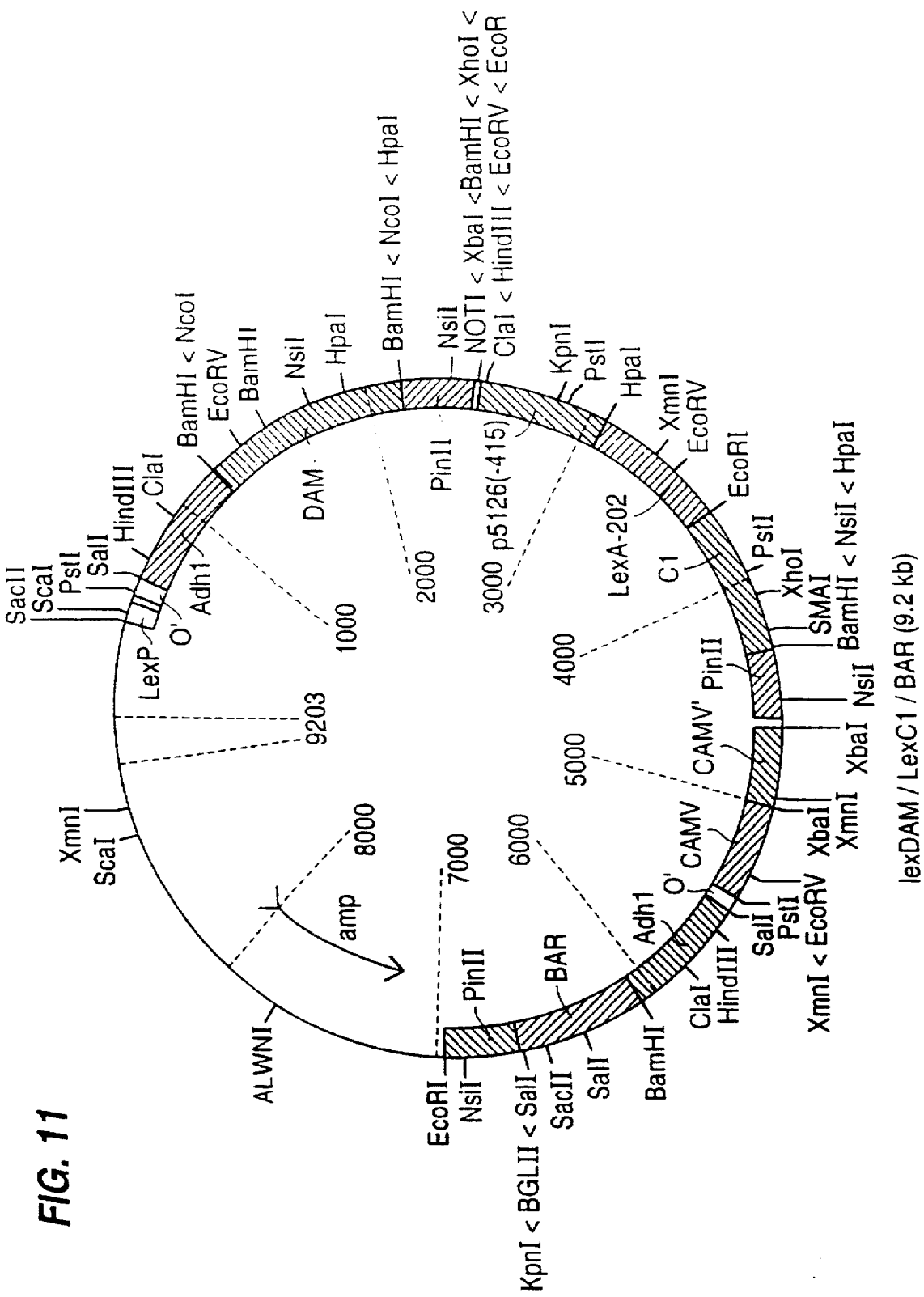
FIG. 11 presents a map of the DP6509 plasmid which contains a lexA binding site with minimal −33 CaMV 35S promoter, Adh1 intron, DAM-methylase and pinII terminator, and which also contains the 5126 promoter fused to lexA202-C1 and a selectable marker construct, CaMV 35S::BAR.

To generate a male-sterile maize plant the DAM-methylase gene is placed under the control of the LexAop fused to the minimal CAMV 35S promoter. Contained on the same plasmid is the 5126::LexA-C1 region and a selectable marker, 35S:BAR (FIG. 11, DP6509). Introduction of this construct renders the plants male-sterile due to the expression of the DAM-methylase gene in the anther. LexA-C1 is regulated by the 5126 promoter.

In order to restore fertility to the male-sterile 5126:LexA-C1, LexAop::DAM-methylase containing plants, such plants are crossed to plants that contain the 5126 promoter or other suitable promoters fused only to the LexA DNA portion. The presence of a genetic construct which includes 5126:LexA is consistent with male fertility. In the presence of a gene that expresses a protein that binds to the LexAop but does not activate transcription of the DAM-methylase gene, synthesis of a DAM-methylase protein is repressed thus the plant is male-fertile.

Transgenic maize plants were generated as described herein to contain plasmids PHP6522, PHP6555 and PHP6520, of the transgenic events that generated transgenic maize plants containing the male-sterility construct PHP6520, 5 events were determined to be male sterile plants in the TO generation and 3 events were determined to be male fertile. 3 of the male sterile events were analyzed in the Ti generation for cosegregation of the male-sterile phenotype with Ignite resistance. The results are shown in Table 1:

TABLE 1

| Event | Ignite-resistant Male Sterile Plants | Ignite-sensitive Male Fertile Plants |
| --- | --- | --- |
| 937.59.35.2 | 17 | 13 |
| 937.63.25.1 | 2 | 28 |
| 937.59.35.1 | 1 | 0 |

The male-sterile events 937.59.35.2 and 937.63.25.1 were crossed by using pollen derived from plants that contain the lexA gene under the control of either the Ubiquitin promoter (PHP6555) or the anther specific promoter (PHP6522), respectively. The result is that plants containing both the sterility construct (PHP6520) and the repressor construct (PHP6522 or 6555) will be male-fertile, whereas plants that contain only the sterility construct PHP6520 will be male-sterile.

Transgenic events were generated as described supra using constructs containing a modified version of the 5126 promoter (the nucleotide sequence from positions–503 to –134 relative to the start codon at position 1488, as shown in FIG. 1) which has embedded the lexA binding site juxtaposed to the minimal CaMV promoter (PHP8036 and PHP8037). Introduction of those constructs renders the resultant plants male-sterile due to expression of the DAM-methylase gene. Such male-sterile plants containing either PHP8036 or PHP8037 are crossed to plants that express the lexA repressor in a constitutive (PHP6555) or tissue specific (PHP6522) fashion. The result is that plants containing both the sterility construct (PHP8036 or PHP8037) and the repressor construct (PHP6522 or PHP6555) will be male-fertile, whereas plants that contain only the sterility constructs PHP8036 or PHP8037 will be male-sterile.

MATERIALS AND METHODS

Subtraction Probe Procedure (from Invitrogen):

Generation of a subtraction cDNA probe was accomplished in a similar manner to the method for generation of a subtraction library. A diagrammatic outline of the method is shown below. In this scheme, labelled cDNA is first synthesized from the induced (message +) pool of mRNA. The resulting cDNA-RNA hybrid is alkali treated to remove the template mRNA and then hybridized to an excess of photobiotinylated mRNA from pool B (message –). The resulting photobiotinylated RNA/cDNA hybrids are complexed with free streptavidin and removed from the hybridization mixture by selective phenol/chloroform extraction. As in the subtraction library procedure, the streptavidin-photobiotinylated nucleic acid complex is extracted leaving the unhybridized (induced) cDNAs behind. The resulting subtracted cDNA probe can be used directly in hybridization blots or for screening libraries.

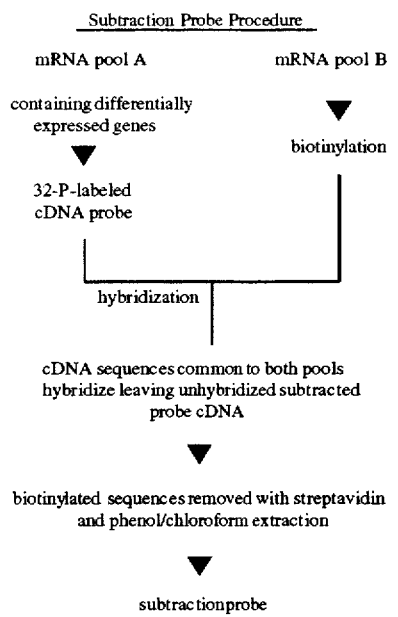

The use of a subtraction cDNA probe improves the chances of identifying cDNA clones that correspond to tissue specific, rare transcripts. In a typical cDNA probe, the representation is proportional to mRNA abundance. By enriching the cDNA probe for sequences specific to a differentially expressed gene, the probe becomes more specific for the intended clone which simplifies the screening of libraries. A subtraction cDNA library can be used in conjunction with a subtracted probe to identify cDNA clones representing low abundance mRNAs unique to a particular tissue or induced cell state. The advantage of using a subtracted cDNA library instead of a non-subtracted cDNA library is that fewer clones have to be screened.

Methods for transient assay: Maize embryogenic suspension cell cultures were derived from immature embryos, maintained in liquid suspension as described (Bowen, 1992) and subcultured every 3 to 4 days. Cells were harvested 2 days after subculture and, prior to bombardment, treated overnight in growth medium containing 0.25M mannitol at a density of 50 mg/ml. For each bombardment, 25 mg of cells was placed on filter paper premoistened with 1 ml of growth medium. 3 µg of reporter plasmid DNA (DP6232) and varying amounts of DP5817 and/or L121 (0.01–3 µg) was precipitated on 0.75 mg of 1.8-µm tungsten particles and the cells were bombarded with one-sixth of this mixture using a PDS1000 helium gun, according to the manufacturer's instructions (DuPont). After 24 hours, the cells were harvested and transferred to 1.5 ml screw cap microcentrifuge tubes and maintained at 4° C. throughout all of the remaining procedures. Samples were homogenized in 0.0 ml GUS lysis buffer (Rao and Flynn, 1990: modified by the omission of all detergents) and cleared by centrifugation. Luciferase assays were performed as described by Callis et al., (1987) using a 10-sec integration time on a luminometer (Model 2010; Analytical Lumenescence, San Diego, Calif.). Protein concentration was determined using a BioRad protein assay kit. Extracts were generally 0.75–1.5 µg of protein per of extract. Luciferase specific activity (lµ/µg) was calculated by measuring the luciferase light units in 25 µl of extract and the value corrected for the corresponding protein concentration per µl of extract. Luciferase activities shown in Table 1 are expressed as an average of three bombardments of each treatment.

Isolation of TA39 Genomic Clones Comprising Sequences Homologous to Microspore-Specific mRNA; TA39 Promoters This example provides methods of isolation of genomic DNA clones comprising sequences homologous to any microspore-specific mRNA for which a nucleic acid probe is available. The approach described is useful for isolating microspore-specific regulatory sequences from any plant species which has microspore-specific mRNA that is homologous to such an available probe.

A tobacco anther-specific cDNA clone, TA39, was obtained from Dr. Robert Goldberg of UCLA. TA39 hybridizes to mRNA from anthers in a similar temporal pattern as seen with several tapetum-specific transcripts (Kultunow et al., 1990). In situ hybridizations showed that TA39 is present at low levels in microspores and connective tissue during stage −1 to +1 and then at higher levels in the tapetum from stage 1 through 6 (Goldberg et al., 1993).

A genomic library of a selected plant, for instance a commercially available library of DNA fragment from N. tabacum, var. NK326 (Clontech Laboratories, Inc., Palo Alto, Calif.; catalog FL1070D), partially digested with MboI and cloned into the plasmid EMBL-3, was screened for clones having homology to cDNA clone TA39. Standard hybridization methods were used, such as are described in Sambrook et al., 1989. Candidate clones were purified by three or more cycles of picking plaques, replating, and reprobing with a TA39 cDNA insert, until consistently hybridizing plaques were either purified or shown not be present.

Two distinguishable families of genomic tobacco DNA clones related to the TA39 cDNA clone were identified, each represented by two overlapping clones within each family. One clone of each family was selected for detailed characterization, designated clones 8B3 and 14B1. The region of homology with TA39 in each of these genomic clones, as well as the regions immediately upstream and downstream of these regions of homology, were mapped by restriction enzyme cleavage analysis and DNA hybridization.

These coding sequences and associated 5' presumptive regulatory regions were isolated as subclones and then further subcloned for sequencing. Thus, nested sets of deletions of each genomic clone were produced by using exoIII and mung bean nucleases supplied in a kit by Stratagene. The nested deletions were sequenced by the dideoxy chain termination method of Sanger with an automated DNA sequencer (Applied Biosystems 373A) at the Nucleic Acids Facility of the Iowa State University. The cDNA insert of TA39 was also sequenced for comparison. Within the region of homology with the TA39 cDNA of a microspore-specific mRNA, genomic clone 8B3 is completely homologous with TA39, while the comparable portion of genomic clone 14B1 is about 90% homologous with TA39.

The starting points for transcription of the 14B1 and 8B3 genomic clones were mapped by primer extension experiments to a single nucleotide, 83 bases upstream of the putative translational start site. A perfect TATA box appears 31 bp upstream of the mapped start of transcription in each clone, and a major open reading frame of 110 amino acids is intact downstream of the start of transcription in both clones (i.e., at the position designated "+83" relative to the transcription initiation site). Both clones also have a polyadenylation recognition site, 29 bp and 37 bp downstream of a translational stop codon in clones 14B1 and 8B3, respectively.

Transformation Methods.

Transformation methods for dicots include a number of different well-known methods for direct DNA delivery. Preferred is particle biolistics bombardment of leaf explants. Other methods include Agrobacterium delivery to explants; Agrobacterium cocultivation of protoplasts; electroporation; PEG uptake or other direct DNA delivery into protoplasts and the like. A preferred method for monocots such as corn is delivery of DNA to the treated cells by bombardment, but other methods such as electroporation can also be used.

Cells of a plant are transformed with the foreign DNA sequence of this invention in a conventional manner. If the plant to be transformed is susceptible to Agrobacterium infections, it is preferred to use a vector containing the foreign DNA sequence, which is a disarmed Ti-plasmid. The transformation can be carried out using procedures described, for example, in EP 0 116 718 and EP 0 270 822. Preferred Ti-plasmid vectors contain the foreign DNA sequence between the border sequences, or at least located upstream of the right border sequence. Other types of vectors can be used for transforming the plant cell, using procedures such as direct gene transfer (see, for instance, EP 0 237 356, PCT publication WO/85/01856 and EP 0 275 069); in vitro protoplast transformation as described, for example, in U.S. Pat. No. 4,684,611; plant virus-mediated transformation as taught in EP 0 067 553 and U.S. Pat. No. 4,407,956, for example; and liposome-mediated transformation as described in U.S. Pat. No. 4,536,475, among others.

If the plant to be transformed is corn, recently developed transformation methods are suitable such as the methods described for certain lines of corn by Fromm et al., 1990, and Gordon-Kamm et al., 1990.

If the plant to be transformed is rice, recently developed transformation methods can be used such as the methods described for certain lines of rice by Shimamoto et al., 1990, Datta et al., 1990, Christou et al., 1991, and Lee et al., 1991.

If the plant to be transformed is wheat, a method analogous to those described above for corn or rice can be used. Preferably for the transformation of a monocotyledonous plant, particularly a cereal such as rice, corn or wheat, a method of direct DNA transfer, such as a method of biolistic transformation or electroporation, is used. When using such a direct transfer method, it is preferred to minimize the DNA that is transferred so that essentially only the DNA sequence of this invention, the QM maize gene and associated regulatory regions, is integrated into the plant genome. In this regard, when a DNA sequence of this invention is constructed and multiplied in a plasmid in a bacterial host organism, it is preferred that, prior to transformation of a plant with the DNA sequence, plasmid sequences that are required for propagation in the bacterial host organism, such as on origin of replication, an antibiotic resistance gene for selection of the host organism, and the like, be separated from the parts of the plasmid that contain the foreign DNA sequence.

TUNGSTEN/DNA PROTOCOL FOR DUPONT HELIUM GUN (PARTICLE BIOLISTIC BOMBARDMENT METHOD OF TRANSFORMATION)

Weigh 60 mg 1.8 μm tungsten: put into 15 ml centrifuge tube
Add 2 ml 0.1M $HnO_3$: Sonicate on ice for 20 minutes
Withdraw $HNO_3$: Add 1 ml sterile deionized water and transfer sample to a 2 ml Sarstedt tube. Sonicate briefly
Centrifuge to pellet particles
Withdraw $H_2O$: Add 1 ml 100% EtOH—Sonicate briefly
Centrifuge to pellet particles
Withdraw $H_2O$: Add 1 ml 100% EtOH—Sonicate briefly
Centrifuge to pellet particles Withdraw EtOH. Add 1 ml sterile deionized water.
Sonicate.
Pipet 250 µl of suspension into 4, 2 ml tubes.
Add 750 µl of sterile deionized H$_2$O to each tube.
Freeze tungsten sample between use.
Pipet 50 µl tungsten/H$_2$O suspension into 1.5 ml tube (Sonicate first)
Add 10 µg DNA. Mix
Add 50 µl 2.5M CaCl$_2$. Mix
Add 20 µl 0.1M Spermidine. Mix
Sonicate briefly. Centrifuge for 10 seconds at 10,000 RPM.
Withdraw supernatant. Add 250 µl 100% EtOH. Sonicate briefly.
Centrifuge at 10,000 RPM for 10 seconds
Withdraw supernatant. Add 60 µl 100% EtOH.
Transformation of maize:

Friable embryogenic Type II callus (Armstrong, 1991) was initiated from 1–2mm zygotic embryos isolated from A188 plants pollinated with B73, and maintained as described in Register et al., 1994. Callus was cultured biweekly for 4–6 months prior to transformation. For transformation the callus was suspended in liquid culture medium and sieved through a 710 µm filter mesh, resuspended at a density of 40 µg/ml. 200 mg callus cells were distributed evenly on a glassfiber filter and used for particle bombardment as described in Register et al., 1994, except that 1.0 µm tungsten particles were used in place of gold. Transformant selection and plant regeneration was performed as described in Register, et al.; however, the concentration of bialophos was elevated to 3 mg/L in all appropriate culture media.

Protocol For Corn Transformation to Recover Stable Transgenic Plants

Day - 1 Cells are placed in liquid media and sieved (710 um). 100–200 mg of cells are collected on 5.5 cm glass fiber filter over an area of 3.5 cm. Cells are transferred to media and incubated overnight.

Day - 8 Filter and cells are removed from media, dried and bombarded. Filter and cells are placed back on media.

Day - 5 Cells on the filter are transferred to selection media (3 mg bialophos).

Day - 12 Cells on the filter are transferred to fresh selection media.

Day - 19 Cells are scraped from the filter and dispersed in 5 ml of selection media containing 8.6% low melting point sea agarose. Cells and media are spread over the surface of two 100 mm×15 mm plates containing 20 ml of gel-rite solidified media.

Day - 40 Putative transformants are picked from plate.

Day - 61 Plates are checked for new colonies.

CITED DOCUMENTS

An, G., Mitra, A., Choi, H. K., Costa, M. A., An, K., Thornburg, R. W., and Ryan, C. A. (1989). Functional analysis of the 3' control region of the potato wound-inducible proteinase inhibitor II gene. Plant Cell 1:115–122.

Armstrong, C. L., Green C. E., and Phillips, R. L., (1991). Development and availability of germplasm with high type II culture formation response. Maize Genetics Cooperative Newsletter. 65:92.

Bellomy, G. and Record, M. Jr. (1989) Biotechniques 7:1.

Brooks, J. E., Blumenthal, R. M., and Gingeras, T. R., (1993). The isolation and characterization of the *Escherichia coli* DNA adenine methylase (DAM) gene. Nucl Acids Res. 11:837–851.

Bowen, B. (1992). Anthocyanin genes as visual markers in transformed maize tissues. In GUS Protocols: Using the GUS Gene as a Reporter of Plant Gene Expression. S. R. Gallagher, ed. (New York: Academic Press, Inc.), pp. 163–177.

Brent, R. and Ptashne, M. (1985) A eukaryotic transcriptional activator bearing the DNA specificity of a prokaryotic repressor. Cell 43; 729–736.

Chen, J. J., Pal, J. K., Petryshyn, R., Kuo, I., Yang, J. M., Throop, M. S., Gehrke, L. and London, I. M. (1991). Eukaryotic translation initiation kinases. PNAs 88, 315–319.

Colasanti, J., Tyers, M. and Sundaresan, V., 1991. Isolation and Characterization of cDNA clones encoding a functional P34 cdc2 homologue from Zea mags PNAs 88, 3377–3381.

Czako, M. and An, G. (1991) Expression of DNA coding for Diptheria toxin Chain A is toxic to plant cells. Plant Physiol. 95 687–692.

Dennis, E., Gerlach W., Pryor, A., Bennetzen, J., Inglis, A., Llewellyn, D., Sachs, M., Ferl, R., and Peacock, W. (1994). Molecular characterization of the maize Adh1 gene. Nucl. Acids Res. 12:3983-3990.

DeWet,J. R., Wood, K. V., DeLuca, M., Helinski, D. R., and Subramani, S. (1987). Firefly luciferase gene: Structure and expression in mammalian cells. Mol. Cell. Biol. 7:25–737.

Droge, W., Broer, I., and Puhler, A. (1992) Transgenic plants containing the phoshinothricin-N-acetyltransferase gene metabolize the herbicide L-phosphinothricin (glufosinate) differently from untransformed plants. Planta 187:142–151.

Farmer, A. A., Loftus, T. M., Mills, A. A., Sato, K. V., Neill, J., Yang, M., Tron, T., Trumpower, B. L. and Stanbridge, E.G. (1994) Hum. Mol. Genet. 3, 723–728.

Fromm et al. (1990) Bio/Technology 8:833. Gallie, D. R., Sleat, D. E., Watts J. W., Turner P. C., and Wilson, T. M. A. (1987). The 5'-leader sequence of tobacco mosaic virus RNA enhances the expression of foreign gene transcripts in vitro and in vivo. Nucl. Acids Res. 15:3257–3273.

Gardner, R. C., Howarth, A. J., Hahn, P., Brow-Luedi, M., Shepherd R. J., and Messing, J. C. (1981). The complete nucleotide sequence of an infectious clone of cauliflower mosaic virus by M13mp7 shotgun sequencing. Nucl. Acids Res. 9:2871–2888.

Goff, S. A., Cone, K. C., and Fromm, M. E., (1991). Identification of functional domains in the maize transcriptional activator C1: Comparison of wild-type and dominant inhibitor proteins. Genes Dev. 5,289–309.

Goldberg, R. B., Beals, T. P. and Sanders, P. M., (1993). Anther development: basic principles and practical applications. Plant Cell 5:1217–1229.

Golemis, E. A., and Brent, R. (1992). Fused protein domains inhibits DNA binding by LexA. Mol. & Cell Biol. 12:3006–3014.

Gordon-Kamm et al. (1990) Transformation of maize cells and regeneration of fertile transgenic plants. The Plant Cell 2:603–618.

Herskowitz, J. (1987). Functional inactivation of genes by dominant negative mutations. Nature 329:219–222.

Invitrogen, Subtractor™ / Subtraction Kit for cDNA Probe Generation, Instruction Manual, version 2.3.

Koltunow et al. (1990) "Different temporal and spatial gene expression patterns occur during anther development." Plant Cell 2:1201–1224.

Register, J. C., Peterson, D. J., Bell, P. J., Bullock, W. P., Evans, I. J., Frame, B., Greenland, A. J., Higgs, N. S., Jepson, I., Jiao, S., Lewnau, C. J., Sillick, J. M., and Wilson, H. M. (1994). Structure and function of selectable and non-selectable transgenes in maize after introduction by particle bombardment. Plant Mol. Biol. 25:951-961.

Sambrook, J., Fritsch, E. F., and Maniatis, T. (1989). Molecular Cloning, A Laboratory Manual. Cold Spring Harbor Press.

Shimamoto et al. (1990) Fertile transgenic rice plants regenerated from transformed protoplasts, Nature 338:274.

Su, T. Z., and El-Gewely, M. R., (1988). A multisite-directed mutagenesis procedure using T7 DNA polymerase: Application for reconstructing a mammalian gene. Gene 69:81–89.

Thompson, C. J., Movva, N. R., Tizard, R., Crameri R., Davies, J. E., Lauwereys, M., and Botterman, J. (1987).

Characterization of the herbicide-resistance gene bar from *Streptomyces hygroscopicus*. EMBO J. 6:2519–2523.

EP 0 116 718
EP 0 270 822
EP 0 237 356
EP 0 275 069
EP 0 067 553
WO/85/01856
U.S. Pat. No. 4,684,611
U.S. Pat. No. 4,407,956
U.S. Pat. No. 4,536,475

What is claimed is:

1. A recombinant DNA construct comprising:

a DNA sequence that encodes a gene product which when expressed in a plant inhibits pollen formation or function;

an operator capable of controlling the expression of said DNA sequence;

a gene encoding a DNA binding protein, said DNA binding protein capable of binding to said operator and activating transcription of said DNA sequence that encodes a gene product which, when expressed in a plant, disrupts pollen formation or function; and 5126 promoter or variants, mutants, or derivatives thereof that drive DNA transcription in cells or tissues critical to pollen formation or function operably linked to said gene.

2. A recombinant DNA construct comprising:

(i) a DNA sequence encoding a gene product which when expressed in a plant inhibits pollen formation or function;

(ii) an operator which controls the expression of said DNA sequence; and (iii) a promoter specific to cells critical to pollen formation or function operatively linked to said DNA sequence encoding a gene product, wherein said anther-specific promoter comprises promoter 5126 or variants, mutants, or derivatives thereof that drive DNA transcription in cells or tissues critical to pollen formation or function.

3. A recombinant DNA construct comprising: a DNA sequence encoding a DNA-binding protein and a promoter which controls expression of said DNA sequence, said protein capable of binding to the operator of the recombinant DNA construct of claim 2, wherein said DNA-binding protein is lexA protein.

4. A recombinant DNA construct comprising: a DNA sequence encoding a DNA-binding protein and a promoter which controls expression of said DNA sequence, said protein capable of binding to the operator of the recombinant DNA construct of claim 2, wherein said anther-specific promoter comprises promoter 5126 or variants, mutants, or derivatives thereof that drive DNA transcription in cells or tissues critical to pollen formation or function.

5. A recombinant DNA construct comprising (i) a lexA DNA binding site embedded in a tissue specific promoter which is operatively linked to a dominant negative gene that, when expressed in a plant, disrupts pollen formation of function, and (ii) a lexA repressor encoding DNA sequence operatively linked to an inducible promoter, wherein the tissue specific promoter is promoter 5126 or variants, mutants, or derivatives thereof that drive DNA transcription in cells or tissues critical to pollen formation or function.

6. A recombinant DNA construct comprising: a DNA sequence encoding a DNA-binding protein and a promoter which controls expression of said DNA sequence, said protein capable of binding to the operator of the recombinant DNA construct of claim 1, wherein said promoter comprises 5126 promoter or variants, mutants, or derivatives thereof that drive DNA transcription in cells or tissues critical to pollen formation or function operatively linked to said DNA sequence.

7. A recombinant DNA construct comprising: a DNA sequence encoding a DNA-binding protein and a promoter which controls expression of said DNA sequence, said protein capable of binding to the operator of the recombinant DNA construct of claim 1, wherein said DNA-binding protein is lexA protein.

8. The recombinant DNA construct of claim 2, wherein said operator is lexA operator.

9. The recombinant DNA construct of claim 2, further comprising a selectable marker gene.

10. The recombinant DNA construct of claim 2, wherein said construct is DP5814.

11. The recombinant DNA construct of claim 2, wherein said construct is DP6509.

12. The recombinant DNA construct of claim 2, wherein said construct is PHP8036.

13. The recombinant DNA construct of claim 2, wherein said construct is PHP8037.

14. The recombinant DNA construct of claim 2, wherein said construct is PHP6520.

15. The recombinant DNA construct of claim 4, wherein said construct is PHP6522.

16. The recombinant DNA construct of claim 3, wherein said construct is PHP6555.

17. The recombinant DNA construct of claim 4, wherein said promoter comprises the nucleotide sequence of the Sca-NcoI fragment of DP5055.

18. The recombinant DNA construct of claim 4, wherein said promoter comprises a nucleotide sequence extending at least 503 base pairs upstream relative to the start codon at nucleotide position 1488 of FIG. 1.

19. The recombinant DNA construct of claim 4, wherein said promoter comprises a nucleotide sequence extending from position −503 to position −1 upstream relative to the start codon at nucleotide position 1488 of FIG. 1.

20. The recombinant DNA construct of claim 4, wherein said promoter comprises a nucleotide sequence extending from position −587 to position −1 upstream relative to the start codon at nucleotide position 1488 of FIG. 1.

21. The recombinant DNA construct of claim 4, wherein said promoter comprises a nucleotide sequence extending from position −890 to position −1 upstream relative to the start codon at nucleotide position 1488 of FIG. 1.

22. The recombinant DNA construct of claim 5, wherein said promoter comprises a nucleotide sequence extending from position −503 to position −134 upstream relative to the start codon at nucleotide position 1488 of FIG. 1.

23. The recombinant DNA construct of claim 2, wherein said promoter comprises the nucleotide sequence of the Sca-NcoI fragment of DP5055.

24. The recombinant DNA construct of claim 2, wherein said promoter comprises a nucleotide sequence extending at least 503 base pairs upstream relative to the start codon at nucleotide position 1488 of FIG. 1.

25. The recombinant DNA construct of claim 2, wherein said promoter comprises a nucleotide sequence extending from position −503 to position −1 upstream relative to the start codon at nucleotide position 1488 of FIG. 1.

26. The recombinant DNA construct of claim 2, wherein said promoter comprises a nucleotide sequence extending from position −587 to position −1 upstream relative to the start codon at nucleotide position 1488 of FIG. 1.

27. The recombinant DNA construct of claim 2, wherein said promoter comprises a nucleotide sequence extending from position −890 to position −1 upstream relative to the start codon at nucleotide position 1488 of FIG. 1.

28. The recombinant DNA construct of claim 2, wherein said promoter comprises a nucleotide sequence extending from position −503 to position −134 upstream relative to the start codon at nucleotide position 1488 of FIG. 1.

29. A recombinant DNA construct comprising (i) a DNA sequence encoding a gene product which inhibits pollen formation or function and (ii) a 5126 promoter or variants, mutants, or derivatives thereof that drive DNA transcription in cells or tissues critical to pollen formation or function that is operably linked to said DNA sequence encoding said gene product.

30. The recombinant DNA construct of claim 29, wherein said gene product is an exogenous methylase gene.

31. The method of claim 5, wherein the inducible promoter is induced by a chemical herbicidal safener.

32. The recombinant DNA construct of claim 5, wherein the dominant negative gene is DAM-methylase.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
( A ) LENGTH: 1490 base pairs
( B ) TYPE: nucleic acid
( C ) STRANDEDNESS: double
( D ) TOPOLOGY: linear ( x i ) SEQUENCE DESCRIPTION: SEQ ID NO:1:

```
TTTTTATCTT TCTGATTTCA ACCATTACCG ATGAATTTCT ATTTGGATTA GTTCATTTTC       60
GTCTTCCCTG TCTGATCCTG TTTTCGACAA TTCTGATCCC GAATCCGTTT TTGAATTAAA      120
ATATAAAAAA TAAAAACAAG AAATGGTTTA TCTCGGTCAA TTTCGTTTTT CGCGAGGAAC      180
ATATTCGGTG TACATGAGCC TTTGGTGCAC ATGAACTAAC AAAGTTCACA AAAAATTCTG      240
AAAAAAAATC ATACATATTC TTTGCATCGC TACTCCTATT ATATATAAAA TTTCATGTTC      300
AAATTTGTTA TATTTTAGCT GTAATAAAAA GAGTATTTTT AGCCGATTTT CTAATTTAAA      360
CTTGTCAGAA GTTGTCTTTT TTATTACAA CTAAGTTTAA TGAATTTGAA CTTGAAACAT       420
GTATATAATT AGAGTAAGAT GAAAAGAATA TGTATGGATT TTTTCAAAAA AATTGTAAAC      480
CTTTTTTAGT TCATGTGCAC CATATGTGAA TCAAAGGTTC ATATACACCG GATATGTTTC      540
CTTTTTCACG AACCTAATCT GGCCTAGCCA GTATGTTGTG GACTTGGCTC CTAAGTGTGA      600
ACCTGGCAGT GATGGGCAAC AAAGCAGGCA TGCCTTATGT GTGATGAATA ATTGACACAT      660
GTACCGAGAG GTTTGGGGTT TTTTTGTATT GCATAGCAAA ACATGGTGAA ATTCTTAGGG      720
TATTTTTGAG ATTACATTTA GGGCATGTTT GTTTCCCTTC ATTTTGAGGA ATTGGAATCT      780
AACTAATAAA TTAGGCTATT TTTTAGAAT GTGACATTCC CAACTTTCTA AAGTGTACAT       840
ATAAGTCTAT CTTAAATAAT TTATAGGGTG GAAGATGTAA ATTGATTATA TAGATTTATA      900
AGCTTCTTTT CTAATGTAAA ATTTAAAGCT CACTCTTCTA CTTGCTTCTC TATAACATAA      960
TATAGTTTAT AACTACCTCT CTCATATGAT TTAGAATAAT ATACAAATAT ATTACATAAA     1020
AAATATATTA ATTGAATTAG TGTTGTCTAA TTTATAATTA TTAGAATGTA ATTCAATTCC     1080
AACGAAACAA CGGGGCCTTA GGTTTAATAT CTTCCTTACA CTGCGAAAAT GTTGTTACAC     1140
TTGCCAAAAA AAATCAATCG CATATTTACC TTACAAGGAC ATATTTTAGC AAAATGCTAT     1200
AGACATGAAT CCAACGTAAT CAATAGAGTG AGATTACTG GTAAACTACC AATTGCTCAT      1260
CTGCTCGGTA CCAACCAGCC TTTCCTATTA CCATGCACAT GTTGCCTCTC AACTGCAGCA     1320
TCTTTCAAGC CGTGAGCAGA CATGTTGCAG ATCGAAGTAA GGTATATATG TGCATAGTCT     1380
```

| CCTAATTCTT | CATCTTCAAC | CTCTAGCTGA | TTGATCTCTG | GTATTACCA | CTCTTTCCTT | 1440 |
| CCTTCCTTCC | TTCAATTCTA | AATACCACAA | ATCAAAGTTG | CTTTGCGATG | | 1490 |

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

TGTAAAACGA CGGCCAGT         18

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CAGGAAACAG CTATGACC         18

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CCTTCATCAG CTTCTGGCAG         20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

AGATCTCGGC CAGGCCCTTG         20

( 2 ) INFORMATION FOR SEQ ID NO:6:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GAGTTGATGA AGTGA         15

( 2 ) INFORMATION FOR SEQ ID NO:7:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

```
GAGATCAATC AGCTAGAGG                                                                      19
```

( 2 ) INFORMATION FOR SEQ ID NO:8:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
TAAACCTAAG GCC                                                                            13
```

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
AATAGCCTAA TTTATTAG                                                                       18
```

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
ACATGTTTCA AGTTCAA                                                                        17
```

( 2 ) INFORMATION FOR SEQ ID NO:11:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
CTTGTCAGAA GTTGTC                                                                         16
```

( 2 ) INFORMATION FOR SEQ ID NO:12:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
CAACCATTAC CGATGAA                                                                        17
```

( 2 ) INFORMATION FOR SEQ ID NO:13:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
ACGAGCGGAC GCACGACAG                                                                      19
```

( 2 ) INFORMATION FOR SEQ ID NO:14:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:14:

TCCGTCGCCA TCTGCGTCAC 20

( 2 ) INFORMATION FOR SEQ ID NO:15:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i x ) FEATURE:
( A ) NAME/KEY: misc_feature
( B ) LOCATION: group(21..22, 26..27, 31..32)
( D ) OTHER INFORMATION: /note= "N represents I"

( x i ) SEQUENCE DESCRIPTION: SEQ ID NO:15:

CACGCGTCGA CTAGTACGGG NNGGGNNGGG NNG 33

( 2 ) INFORMATION FOR SEQ ID NO:16:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO:16:

GCTGCTCACC ATGGCAAAGC AAC 23

( 2 ) INFORMATION FOR SEQ ID NO:17:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( x i ) SEQUENCE DESCRIPTION: SEQ ID NO:17:

CCATGGGGAC AATG 14

( 2 ) INFORMATION FOR SEQ ID NO:18:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( x i ) SEQUENCE DESCRIPTION: SEQ ID NO:18:

ATGAAGAAAA ATCGCGCTTT TTTGAAGTGG GC 32

( 2 ) INFORMATION FOR SEQ ID NO:19:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( x i ) SEQUENCE DESCRIPTION: SEQ ID NO:19:

TCACCCAGGC GGGCAAAATC AGCCGACA  28

( 2 ) INFORMATION FOR SEQ ID NO:20:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

CCGTTAACGC TTTCATGACG CCCGGAATTA AGC  33

( 2 ) INFORMATION FOR SEQ ID NO:21:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

GATCTACTGC TGTATATAAA ACCAGTGGTT ATATGTACAG TACTGCTGTA TATAAAACCA  60
GTGGTTATAT GTACAGTACG GATG  84

( 2 ) INFORMATION FOR SEQ ID NO:22:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:22:

GTAGCCGTAC TGTACATATA ACCACTGCTT TTATATACAG CAGTACTGTA CATATAACCA  60
CTGGTTTTAT ATACAGCA  78

( 2 ) INFORMATION FOR SEQ ID NO:23:

( i ) SEQUENCE CHARACTERISTICS:
        ( A ) LENGTH: 1485 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

GGAATTCGGC ACGAGCTCGG TGCCGCCTTC CTTCCTTCAA TTCTAAATAC CACAAATCAA  60
AGTTGCTTTG CGATGGTGAG CAGCAGCATG GACACGACGA GTGACAAGCG TGCGTCATCC  120
ATGCTGGCCC CTAACCCTGG CAAGGCCACG ATCCTCGCCC TTGGCCACGC CTTCCCGCAG  180
CAGCTTGTCA TGCAGGACTA CGTCGTCGAC GGCTTCATGA AGAACACCAA CTGTGACGAC  240
CCGGAGCTCA AGGAGAAGCT CACCAGACTC TGCAAGACGA CGACCGTGAG GACTCGGTAC  300
GTGGTGATGT CGGATGAGAT CCTCAAGAAC TACCCGGAGC TGGCCCAGGA GGGGCTGCCG  360
ACGATGAACC AGCGTCTGGA CATCTCGAAC GCGGCGGTGA CGCAGATGGC GACGGAGGCG  420
TCCCTGTCGT GCGTCCGCTC GTGGGGCGGC GCGCTCTCGT CCATTACCCA CCTGGTGTAC  480

| | | | | | | |
|---|---|---|---|---|---|---|
| GTCTCGTCGA | GCGAGGCGCG | CTTCCCGGGC | GGCGACCTGC | ACCTGGCGCG | CGCGCTGGGG | 540 |
| CTGAGCCCGG | ACGTCCGCCG | CGTCATGCTG | GCCTTCACCG | GCTGCTCGGG | CGGCGTGGCG | 600 |
| GGGCTCCGCG | TGGCCAAGGG | CCTGGCCGAG | AGCTGCCCGG | GCGCGCGCGT | GCTGCTGGCC | 660 |
| ACCTCCGAGA | CCACCATCGT | GGGGTTCCGC | CCGCCCAGCC | CCGACCGCCC | CTACGACCTC | 720 |
| GTGGGCGTGG | CGCTCTTCGG | CGACGGCGCG | GGCGCCGCCG | TCATCGGCAC | CGACCCCGCC | 780 |
| CCCGCCGAGC | GCCCGCTCTT | CGAGCTCCAC | TCGGCGCTCC | AGCGCTTCCT | CCCGGACACG | 840 |
| GAGAGGACCA | TCGAGGGCCG | GCTGACGGAG | GAAGGCATCA | AGTTCCAGCT | GGGGCGGGAG | 900 |
| CTGCCCCACA | TCATCGAGGC | GCACGTGGAG | GACTTCTGCC | AGAAGCTGAT | GAAGGAGCGG | 960 |
| CAGAGCGGCG | AGGACGCCGA | CGGTGGCGGC | CCCGAGCCGA | TGAGCTACGG | GGACATGTTC | 1020 |
| TGGGCGGTCC | ACCCCGGCGG | GCCGGCCATC | CTAACCAAGA | TGGAGGGGCG | CCTGGGCCTC | 1080 |
| GGCGCCGACA | AGCTCCGCGC | CAGCCGGTGC | GCGCTCCGGG | ACTTCGGCAA | CGCCAGCAGC | 1140 |
| AACACCATCG | TGTACGTGCT | GGAGAACATG | GTGGAGGACA | CCCGGCGGAG | GAGGCTGCTG | 1200 |
| GCTGCTGACG | ACGGTGGAGA | GGACTGCGAG | TGGGGTCTCA | TCCTCGCGTT | CGGGCCGGGG | 1260 |
| ATCACGTTCG | AGGGCATCCT | AGCCAGGAAC | TTGCAGGCAA | CCGCGCGCGC | CTCAGCCCAG | 1320 |
| CTCTGATCAC | CTCTTGCTGT | GTTGCTTTTC | TGCTTGCTCT | GCACCTCTGC | TTCCGTGTGA | 1380 |
| TTGCTGCTTT | GAGGGAGAAT | GCTGAGCATC | AACATTGCTC | ATGAGCATCA | ATGAAATAAG | 1440 |
| GGGCCCCGAA | ATTCACTGCT | CAAAAAAAAA | AAAAAAAAAC | TCGAG | | 1485 |